US 8,492,399 B2

(12) United States Patent
Leadbetter et al.

(10) Patent No.: US 8,492,399 B2
(45) Date of Patent: Jul. 23, 2013

(54) 3-CARBOXYPROPYL-AMINOTETRALIN DERIVATIVES AND RELATED COMPOUNDS AS MU OPIOID RECEPTOR ANTAGONISTS

(71) Applicants: Michael R. Leadbetter, San Leandro, CA (US); Pierre-Jean Colson, San Francisco, CA (US); Miroslav Rapta, San Carlos, CA (US); Ying Yu, Sunnyvale, CA (US)

(72) Inventors: Michael R. Leadbetter, San Leandro, CA (US); Pierre-Jean Colson, San Francisco, CA (US); Miroslav Rapta, San Carlos, CA (US); Ying Yu, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 13/652,808

(22) Filed: Oct. 16, 2012

(65) Prior Publication Data
US 2013/0035510 A1    Feb. 7, 2013

Related U.S. Application Data

(62) Division of application No. 13/330,363, filed on Dec. 19, 2011, now Pat. No. 8,318,765, which is a division of application No. 12/331,659, filed on Dec. 10, 2008, now Pat. No. 8,106,232.

(60) Provisional application No. 61/049,219, filed on Apr. 30, 2008, provisional application No. 61/007,220, filed on Dec. 11, 2007.

(51) Int. Cl.
*A01N 43/42*    (2006.01)

(52) U.S. Cl.
USPC .......................................................... 514/282

(58) Field of Classification Search
None
See application file for complete search history.

(56) References Cited

U.S. PATENT DOCUMENTS 6,498,196 B1    12/2002    Roberts et al.
6,844,368 B1    1/2005    Roberts et al.

FOREIGN PATENT DOCUMENTS

WO    00/37426 A1    6/2000

OTHER PUBLICATIONS

International Search Report for PCT/US2008/086171 dated Jul. 21, 2009.
Grundt et al., "Opioid Binding and in Vitro Profiles of a Series of 4-Hydroxy-3-methoxyindolomorphinans. Transformation of a δ-Selective Ligand into a High Affinity K-Selective Ligand by Introduction of a 5,14-Substituted Bridge", J. Med. Chem., 2003, 46, 3174-3177.
Grundt et al., "Identification of a New Scaffold for Opioid Receptor Antagonism Based on the 2-Amino-1,1-dimethyl-7-hydroxytetralin Pharmacophore", J. Med. Chem., 2004, 47, 5069-5075.
Roy et al., "Synthesis and structure-activity relationship of novel aminotetralin derivatives with high selective opioid affinity", Bioorg & Med Chem Lett, 2002, 12, 3141-3143.
Williams, "Investigation of aminotetralins as novel opioid receptor antagonists", A thesis submitted for the degree of Doctor of Philosophy, University of Bath, May 2006.

*Primary Examiner* — Susanna Moore
*Assistant Examiner* — Jennifer C Sawyer
(74) *Attorney, Agent, or Firm* — Jeffrey A. Hagenah; Roberta P. Saxon

(57) ABSTRACT

The invention provides 3-carboxypropyl-aminotetralin compounds of formula (I):

wherein $R^1$, $R^2$, $R^3$, $R^4$, $R^5$, and $R^6$ are defined in the specification, or a pharmaceutically-acceptable salt thereof, that are antagonists at the mu opioid receptor. The invention also provides pharmaceutical compositions comprising such compounds, methods of using such compounds to treat conditions associated with mu opioid receptor activity, and processes and intermediates useful for preparing such compounds.

4 Claims, No Drawings

3-CARBOXYPROPYL-AMINOTETRALIN DERIVATIVES AND RELATED COMPOUNDS AS MU OPIOID RECEPTOR ANTAGONISTS

CROSS-REFERENCE TO RELATED APPLICATIONS

This application is a divisional application of U.S. Ser. No. 13/330,363, filed Dec. 19, 2011, now allowed, which is a divisional application of U.S. Ser. No. 12/331,659, filed Dec. 10, 2008, now U.S. Pat. No. 8,106,232 B2; which claims the benefit of U.S. Provisional Application Nos. 61/007,220, filed on Dec. 11, 2007, and 61/049,219, filed on Apr. 30, 2008, the disclosures of which are incorporated herein by reference in their entirety.

BACKGROUND OF THE INVENTION

1. Field of the Invention

The invention is directed to 3-carboxypropyl-aminotetralin compounds which are useful as mu opioid receptor antagonists. The invention is also directed to pharmaceutical compositions comprising such compounds, methods of using such compounds for treating or ameliorating medical conditions mediated by mu opioid receptor activity, and processes and intermediates useful for preparing such compounds.

2. State of the Art

It is now generally understood that endogenous opioids play a complex role in gastrointestinal physiology. Opioid receptors are expressed throughout the body, both in the central nervous system and in peripheral regions including the gastrointestinal (GI) tract.

Compounds which function as agonists at opioid receptors, of which morphine is a prototypical example, are the mainstays of analgesic therapy for the treatment of moderate to severe pain. Unfortunately, use of opioid analgesics is often associated with adverse effects on the GI tract, collectively termed opioid-induced bowel dysfunction (OBD). OBD includes symptoms such as constipation, decreased gastric emptying, abdominal pain and discomfort, bloating, nausea, and gastroesophageal reflux. Both central and peripheral opioid receptors are likely involved in the slowdown of gastrointestinal transit after opioid use. However, evidence suggests that peripheral opioid receptors in the GI tract are primarily responsible for the adverse effects of opioids on GI function.

Since the side effects of opioids are predominantly mediated by peripheral receptors, whereas the analgesia is central in origin, a peripherally selective antagonist can potentially block undesirable GI-related side effects without interfering with the beneficial central effects of analgesia or precipitating central nervous system withdrawal symptoms.

Of the three major opioid receptor subtypes, denoted mu, delta, and kappa, most clinically-used opioid analgesics are thought to act via mu opioid receptor activation to exert analgesia and to alter GI motility. Accordingly, peripherally selective mu opioid antagonists are expected to be useful for treating opioid-induced bowel dysfunction. Preferred agents will demonstrate significant binding to mu opioid receptors in vitro and be active in vivo in GI animal models.

Postoperative ileus (POI) is a disorder of reduced motility of the GI tract that occurs after abdominal or other surgery. The symptoms of POI are similar to those of OBD. Furthermore, since surgical patients are often treated during and after surgery with opioid analgesics, the duration of POI may be compounded by the reduced GI motility associated with opioid use. Mu opioid antagonists useful for treating OBD are therefore also expected to be beneficial in the treatment of POI.

SUMMARY OF THE INVENTION

The invention provides novel compounds that possess mu opioid receptor antagonist activity and intermediates for the preparation thereof.

Accordingly, the invention provides a compound of formula (I):

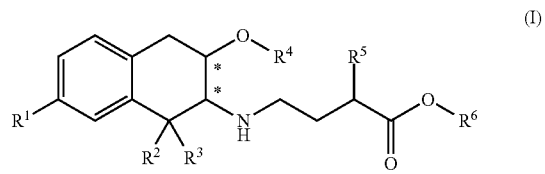

wherein
R$^1$ is —OR$^a$ or —C(O)NR$^b$R$^c$;
R$^2$, R$^3$, and R$^4$ are each independently C$_{1-3}$alkyl;
R$^5$ is selected from C$_{1-6}$alkyl, phenyl, cyclohexyl, —(CH$_2$)$_{1-3}$-cyclohexyl, and —(CH$_2$)$_{1-3}$-phenyl;
R$^a$, R$^b$, and R$^c$ are each independently hydrogen or C$_{1-3}$alkyl; and
R$^6$ is hydrogen or C$_{1-3}$alkyl; and
wherein the substituents at the chiral centers marked by asterisks are in the trans configuration;
or a pharmaceutically-acceptable salt thereof.

The invention also provides a pharmaceutical composition comprising a compound of the invention and a pharmaceutically-acceptable carrier.

The invention also provides a method of treating a disease or condition associated with mu opioid receptor activity, e.g. a disorder of reduced motility of the gastrointestinal tract such as opioid-induced bowel dysfunction and post-operative ileus, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt thereof, as a research tool for studying a biological system or sample or for discovering new compounds having mu opioid receptor activity, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with mu opioid receptor activity, e.g. a disorder of reduced motility of the gastrointestinal tract, in a mammal.

DETAILED DESCRIPTION OF THE INVENTION

The invention provides 3-carboxypropyl-aminotetralin mu opioid receptor antagonists of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, $R^1$ is —$OR^a$ or —$C(O)NR^bR^c$.

In another specific aspect, $R^1$ is —OH or —$C(O)NH_2$.

In yet another specific aspect, $R^1$ is —$C(O)NH_2$.

In a specific aspect, $R^2$, $R^3$, and $R^4$ are each independently $C_{1-3}$alkyl.

In another specific aspect, $R^2$ and $R^3$ are each independently methyl or ethyl.

In yet other aspects, $R^2$ and $R^3$ are each ethyl; or $R^2$ and $R^3$ are each methyl.

In a specific aspect, $R^4$ is methyl.

In a specific aspect, $R^5$ is selected from $C_{1-6}$alkyl, phenyl, cyclohexyl, —$(CH_2)_{1-3}$-cyclohexyl, and —$(CH_2)_{1-3}$-phenyl.

In another specific aspect, $R^5$ is selected from $C_{3-5}$alkyl, cyclohexyl, —$(CH_2)_{1-3}$-cyclohexyl, and —$(CH_2)_{1-3}$-phenyl. Representative $R^5$ groups within this aspect include, but are not limited to, n-pentyl, n-butyl, 2,2-dimethylpropyl, 2-methylpropyl, 1-methylethyl, cyclohexyl, cyclohexylmethyl, 4-phenylbutyl, and phenylmethyl.

In yet another specific aspect, $R^5$ is cyclohexylmethyl.

In a specific aspect, $R^6$ is hydrogen or $C_{1-3}$alkyl.

In another aspect, $R^6$ is hydrogen, i.e. the compounds are carboxylic acids.

The carboxylic acids of the invention have been shown to be potent antagonists at the mu opioid receptor.

In still other aspects, $R^6$ is $C_{1-3}$alkyl, or $R^6$ is methyl, i.e. the compounds are esters.

As described below, the esters of the invention are useful intermediates for the preparation of the carboxylic acids of the invention. In addition, the ester compounds in which $R^1$ is —$C(O)NH_2$, $R^2$ and $R^3$ are each ethyl, $R^4$ is methyl, $R^5$ is 2-methylpropyl or cyclohexylmethyl, and $R^6$ is methyl have been shown to be potent antagonists at the mu opioid receptor.

The invention further provides the compounds of Examples 1-16 herein.

The chemical naming convention used herein is illustrated for the compound of Example 1

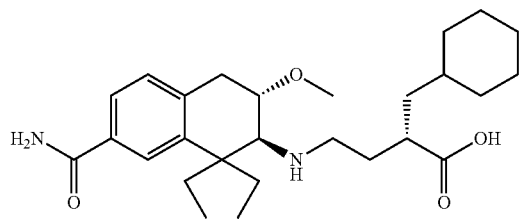 [SMILES: CCC1(CC)c2cc(C(N)=O)ccc2C[C@H](OC)[C@H]1NCC[C@H](CC1CCCCC1)C(=O)O]

which is (S)-4-(2S,3S)-7-carbamoyl-1,1-diethyl-3-methoxy-1,2,3,4-tetrahydronaphthalen-2-ylamino)-2-(cyclohexylmethyl)butyric acid according to the IUPAC conventions as implemented in AutoNom software, (MDL Information Systems, GmbH, Frankfurt, Germany). For convenience, the bicyclic 1,2,3,4-tetrahydronaphthalen-2-ylamino group is alternatively referred to herein, by the common name, "aminotetralin".

All of the compounds of the invention are in the trans configuration with respect to the two chiral centers indicated by asterisks in formula (I):

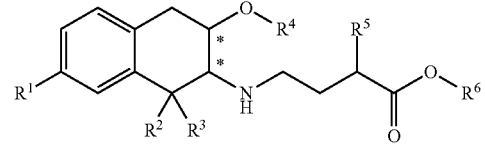

In addition to the stereochemistry of the aminotetralin group, the compounds of the invention may contain a chiral center at the carbon atom to which the substituent $R^5$ is attached. The compounds may be a pure diastereomer, for example, the (2S),(3S) diastereomer of the compound of Example 1 depicted above, or a mixture of the (2S),(3S) diastereomer and the (2R),(3R) diastereomer. Such diastereomeric mixtures are denoted herein by the prefix trans. Accordingly, the invention includes pure diastereomers, mixtures of diastereomers, racemic mixtures, and stereoisomer-enriched mixtures of isomers, unless otherwise indicated. When the stereochemistry of a compound is specified, it will be understood by those skilled in the art, that minor amounts of other stereoisomers may be present in the compositions of the invention unless otherwise indicated, provided that any utility of the composition as a whole is not eliminated by the presence of such other isomers.

In another aspect, the invention provides a compound of formula (Ia):

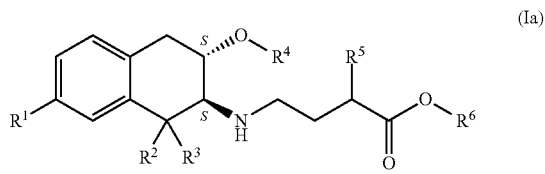

wherein the stereochemistry at the chiral centers is (2S),(3S) and wherein $R^1$, $R^2$, $R^3$, $R^4$, $R^5$, and $R^6$ take any of the values described above.

In a particular aspect, the invention provides a compound of formula (Ia) wherein:

$R^1$ is —$C(O)NH_2$;

$R^2$ and $R^3$ are each ethyl;

$R^4$ is methyl;

$R^5$ is selected from $C_{3-5}$alkyl, cyclohexyl, —$(CH_2)_{1-3}$-cyclohexyl, and —$(CH_2)_{1-3}$-phenyl; and $R^6$ is hydrogen or methyl;

or a pharmaceutically-acceptable salt thereof.

When administered to a mammal, medical compounds are typically transformed in the body by metabolism to forms which can be excreted. As described in the example section below, metabolic transformation of the present compounds has been investigated by incubating a compound of the invention with cryopreserved human hepatocytes and comparing the resulting metabolites with compounds of known structure. Results obtained support the conclusion that a principal hydroxyl metabolite of the compound of Example 1 is substituted with hydroxyl at the 4-position of the cyclohexyl ring.

In yet another aspect, therefore, the invention provides a compound of formula (Ib) wherein R is hydroxyl:

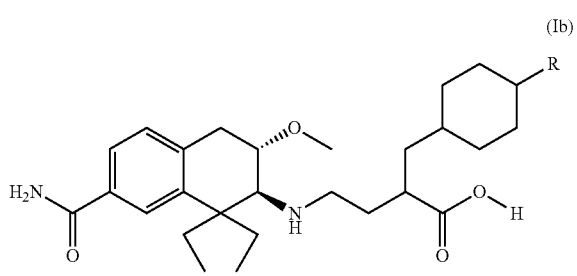

wherein the compound of formula (Ib) wherein R is hydroxyl is produced in vivo by administering to a human a compound of formula (Ib) wherein R is hydrogen.

DEFINITIONS

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "compound" means a compound that was synthetically prepared or prepared in any other way, such as by in vivo metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes one or more of the following:
(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient, including counteracting the effects of other therapeutic agents;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In a typical method of synthesis, the esters of the invention of formula (I) in which $R^6$ is a $C_{1-3}$ alkyl are prepared as shown in Scheme A. (The substituents and variables shown in the following schemes have the definitions provided above unless otherwise indicated).

Scheme A

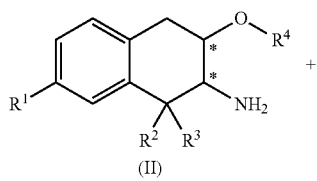

Scheme B

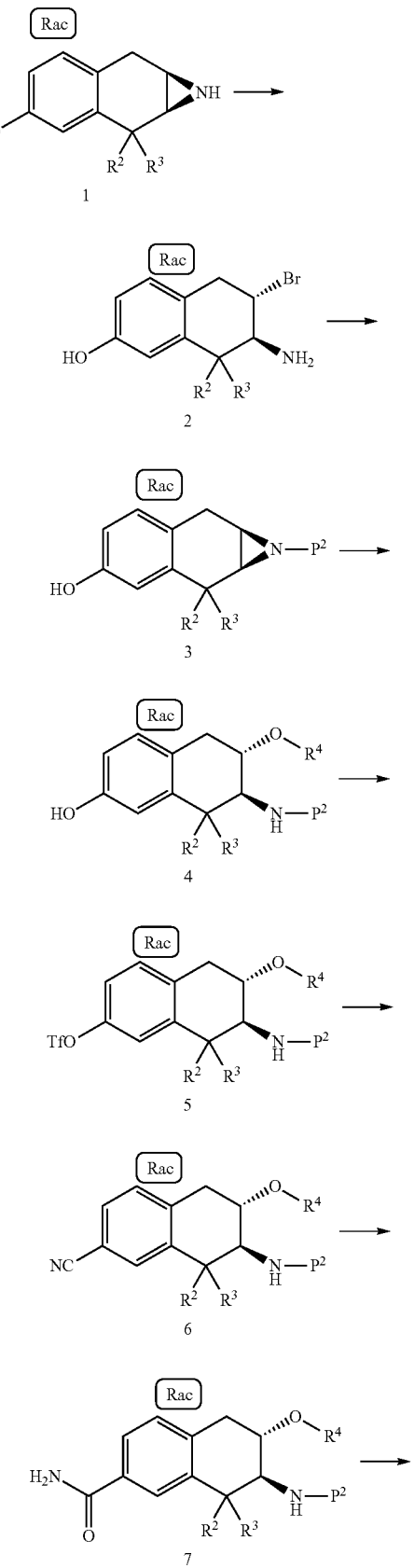

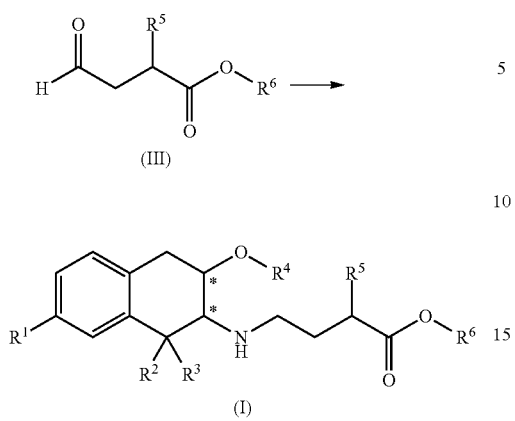

In Scheme A, intermediate (II) is reductively N-alkylated by reaction with the aldehyde (III) to provide the product (I). The reaction is typically conducted by contacting intermediate (II) with between about 1 and about 2 equivalents of an aldehyde of formula (III) in a suitable inert diluent, such as dichloromethane, methanol, or 2-methyltetrahydrofuran, in the presence of between about 1 and about 5 equivalents of a reducing agent. The reaction is typically conducted at a temperature in the range of about 0° C. to ambient temperature for about a half hour to about 3 hours or until the reaction is substantially complete. Typical reducing agents include sodium triacetoxyborohydride, sodium borohydride, and sodium cyanoborohydride.

The aldehyde (III) may be generated in situ from the corresponding bisulfite adduct (III'):

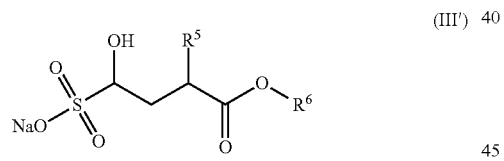

by reaction with a base such as sodium hydroxide immediately prior to reaction with the aminotetralin (II).

The carboxylic acids of the invention of formula (I) in which $R^6$ is hydrogen are prepared from the above esters by contacting the corresponding ester with an excess of base, for example between about 4 and about 6 equivalents of a base such as sodium hydroxide in methanol. The reaction is conducted at a temperature of between about 25 and about 50° C. for between about 2 and about 24 hours or until the reaction is substantially complete.

Alternatively, a carboxylic acid of the invention can be prepared by a process in which a hydroxy-protecting group is used at $R^6$ and which includes a final deprotection step, as described in Example 17 below.

An exemplary procedure for the preparation of an aminotetralin intermediate (II) in which the variable $R^1$ is —C(O)NH$_2$ is illustrated in Scheme B

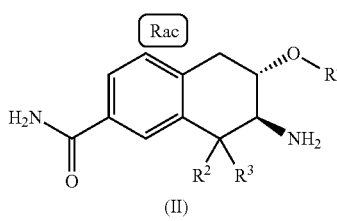

(II)

where P¹ represents a hydroxy-protecting group, P² represents an amino-protecting group, and —OTf represents trifluoromethane sulfonate (commonly triflate). The notation "Rac" indicates the compound is a racemic mixture of the particular structure depicted and the structure having the opposite stereochemistry at the chiral centers.

A small alkyl is useful as the protecting group P¹. Using an alkyl for P¹, aziridine intermediate 1, can be reacted with HBr to provide intermediate 2 which is conveniently isolated in solid form as the HBr salt. Typically intermediate 1 is contacted with an excess, for example between about 12 and about 18 equivalents, of HBr. The efficiency of the reaction is improved by inclusion of a phase transfer catalyst. The reaction is typically conducted at a temperature between about 90 and about 110° C. for between about 10 and about 20 hours or until the reaction is substantially complete. Using Boc, for example, for the protecting group P², intermediate 3 is then formed by treating 2 with base, which reforms the aziridine ring in situ, and adding between about 1 and about 1.3 equivalents of di-tert-butyldicarbonate (commonly (Boc)₂O) under conventional reaction conditions to provide intermediate 3.

Alternatively, the P¹ group of aziridine intermediate 1 is deprotected in two steps by reaction with HBr or BBr₃ and subsequent treatment with base to provide intermediate 2a:

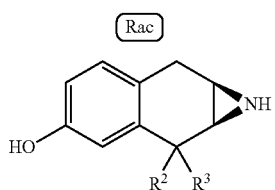

2a which is then protected at the aziridine nitrogen, for example by reaction with (Boc)₂O to provide intermediate 3.

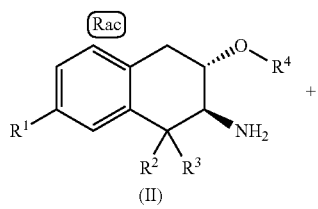

(II)

Next, the amino-protected aziridine 3 is contacted with a large excess of an alcohol R⁴OH in the presence of a mild acid catalyst, such as pyridium tosylate to provide intermediate 4.

An aminotetralin intermediate of formula (II) in which R¹ is —OH can be prepared by deprotection of intermediate 4. For example, when the protecting group P² is Boc, the phenol intermediate of formula (II) is obtained by treating 4 with an acid. Similarly, an aminotetralin intermediate of formula (II) in which R¹ is —ORᵃ where Rᵃ is $C_{1-3}$alkyl, can be prepared analogously starting with an intermediate of formula 1 in which P¹ is the desired small alkyl and omitting the initial deprotection step.

The remainder of the steps in Scheme B depict the conversion of the hydroxy substituted aminotetralin 4 to a carboxamide substituted intermediate 7 and a final deprotection step. The hydroxyl of intermediate 4 is first converted to the triflate by contacting 4 in an inert diluent with between about 1 and about 2 equivalents of trifluoromethane sulfonylchloride in the presence of between about 1 and about 3 equivalents of base, such as triethylamine to provide intermediate 5. Reaction of 5 with zinc cyanide in the presence of a transition metal catalyst, provides intermediate 6. This reaction is typically conducted at a temperature between about 80° C. and 120° C. under an inert atmosphere for about one half to about 2 hours or until the reaction is substantially complete.

Next, the nitrile of intermediate 6 is hydrolyzed to the carboxamide of intermediate 7. As described in the examples below, in one method of synthesis, the nitrile 6 is contacted with between about 5 and about 8 equivalents of sodium perborate monohydrate in an inert diluent such as methanol. The reaction is conducted at a temperature between about 50 and about 60° C. for about 12 to about 24 hours or until the reaction is substantially complete. Alternative processes for hydrolysis of a nitrile to an amide include use of a platinum catalyst, in particular, hydrido(dimethylphosphoniousacid-kP)[hydrogen bis(dimethylphosphinito-kP)]platinum(II), and treatment with hydrogen peroxide, as described in examples below. Finally, intermediate 7 is deprotected by conventional treatment with an acid to provide the aminotetralin of formula (II).

An intermediate of formula (II) in which R¹ is —C(O)NRᵇRᶜ where Rᵇ and Rᶜ are alkyl can be prepared from intermediate 6 by converting the nitrile to a carboxylic acid by hydrolysis in the presence of a base followed by amide coupling with an amine of the formula HNRᵇRᶜ.

The individual enantiomers of formula (II) can be separated using a chiral auxiliary. Scheme C illustrates use of the chiral auxiliary carbonic acid 4-nitro-phenyl ester (R)-1-phenyl-ethyl ester (8):

Scheme C

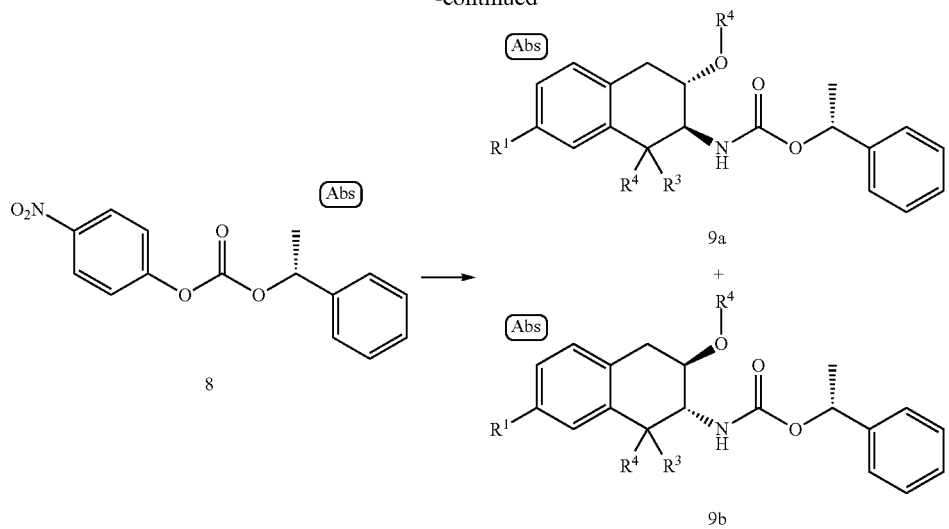

to prepare a pair of non-racemic diastereomers 9a and 9b that can be separated. The notation "Abs" denotes the specific chiral compound shown. The racemic aminotetralin (II) is contacted with between about 0.8 and about 1.2 equivalents of chiral auxiliary 8 in an inert diluent in the presence of between about 2 and about 4 equivalents of a base, such as triethylamine to prepare a diastereomeric mixture of intermediates 9a and 9b. The reaction is typically conducted at a temperature between about 80 and about 95° C. for between about 4 and about 20 hours or until the reaction is substantially complete. The diastereomers 9a and 9b can be separated by high performance liquid chromatography (HPLC) and collected separately or by crystallization in which the diastereomer 9a crystallized preferentially, leaving predominantly the diastereomer 9b in solution. Finally, the carbamate group can be removed from the isolated 9a and 9b diastereomers by treatment with an acid to provide the individual enantiomers of aminotetralin (II). The chiral auxiliary 8 can be prepared by reaction of (R)-1-phenylethanol with p-nitrophenyl chloroformate as described in the examples below.

The aziridine intermediate 1 used in Scheme B can be obtained by reacting a substituted 3,4-dihydro-1H-naphthalen-2-one:

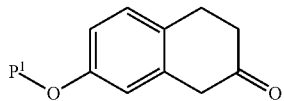

with an alkyl halide to add the alkyl substituents $R^2$ and $R^3$ at the 2-position, treatment with a hydroxylamine salt to convert the carboxy to an oxime and subsequent treatment with lithium aluminum hydride or other reducing agent to convert the oxime to the aziridine 1, as described, for example, in U.S. Pat. No. 6,844,368 and in Preparation 14, below.

The aldehyde (III) used in Scheme A is conveniently prepared from the corresponding carboxylic acid 10 as shown in Scheme D:

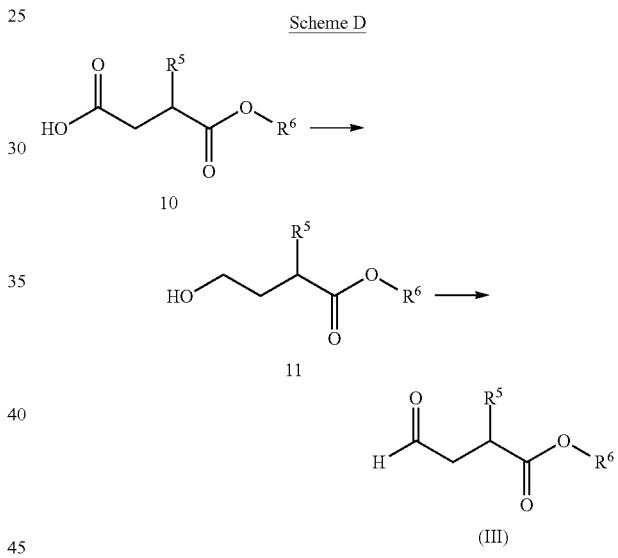

where $R^6$ represents a $C_{1-3}$alkyl. Borane reduction of the carboxylic acid 10 provides the alcohol 11. The reaction is typically conducted by contacting acid 10 with about 2 equivalents of a borane-tetrahydrofuran complex in tetrahydrofuran at a temperature between about −5 and about 0° C. The alcohol 11 is then oxidized to the aldehyde (III). Useful oxidizing reagents include dimethylsulfoxide activated by a sulfur trioxide pyridine complex and sodium hypochlorite with a 2,2,6,6-tetramethylpiperidin-1-oxyl (TEMPO) catalyst. If desired, the alcohol 11 can be converted to the bisulfite adduct (III') without isolation of the aldehyde (III) by addition of sodium bisulfite after the oxidation step.

Further details regarding specific reaction conditions and other procedures for preparing representative compounds of the invention or intermediates thereto are described in the examples below.

Accordingly, in a method aspect, the invention provides a process for preparing a compound of formula (I), or a salt thereof, the process comprising (a) reacting a compound of formula (II) with a compound of formula (III), wherein $R^6$ is $C_{1-3}$alkyl, and, (b) when $R^6$ is hydrogen, contacting the product of step (a) with an excess of base to provide a compound of formula (I), or a salt thereof.

In yet other aspects, the invention provides the novel intermediate of formula 2 or a hydrobromide salt thereof and a process for the preparation of the hydrobromide salt of compound 2 in solid form, the process comprising reacting a compound of formula 1 with HBr and isolating the product in solid form.

Pharmaceutical Compositions

The 3-carboxypropyl-aminotetralin compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired. When discussing compositions, the "compound of the invention" may also be referred to herein as the "active agent". As used herein, the term "compound of the invention" is intended to include compounds of formula (I) as well as the species embodied in formula (Ia). "Compound of the invention" includes, in addition, pharmaceutically-acceptable salts and solvates of the compound unless otherwise indicated.

The pharmaceutical compositions of the invention typically contain a therapeutically effective amount of a compound of the present invention or a pharmaceutically-acceptable salt thereof. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially in any order.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein.

Alternatively, the therapeutic agents may remain separate and distinct before administration to the patient. In this embodiment, the agents are not physically mixed together before administration but are administered simultaneously or at separate times as separate compositions. When administered separately, the agents are administered sufficiently close in time so as to provide a desired therapeutic effect. Such compositions can be packaged separately or may be packaged together as a kit. The two therapeutic agents in the kit may be administered by the same route of administration or by different routes of administration.

In particular, the compounds of the invention can be combined with opioid analgesic therapeutic agents. As described above, use of opioid analgesics is often associated with undesirable side effects such as, for example, constipation, decreased gastric emptying, abdominal pain, bloating, nausea, and gastroesophageal reflux. These adverse effects may be sufficiently severe to limit the dose of opioid analgesic that can be delivered to a patient to a suboptimal level. Coadministration of a compound of the invention with an opioid is likely to reduce or prevent side effects, thereby increasing the utility of the analgesic agent for pain alleviation.

Opioid analgesics that may be used in combination with compounds of the present invention include, but are not limited to, morphine, hydromorphone, oxymorphone, pethidine, codeine, dihydrocodeine, oxycontin, oxycodone, hydrocodone, sufentanil, fentanyl, remifentanil, buprenorphine, butorphanol, tramadol, methadone, heroin, propoxyphene, meperidine, levorphenol, pentazocine, and combinations of opioid analgesics with ibuprofen or acetaminophen. Compounds of the invention could be used in doses ranging from about 0.05 to about 100 mg per day for an average 70 kg patient, when combined with an opioid analgesic at its therapeutic dose, for example, when combined with oxycodone at a dose of between about 5 mg and about 160 mg per day.

In addition, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, or 4-(4-{[(2-isopropyl-1H-benzoimidazole-4-carbonyl)amino]methyl}-piperidin-1-ylmethyl)piperidine-1-carboxylic acid methyl ester may be used as the second therapeutic agent.

Additional useful prokinetic agents include, but are not limited to, 5-HT$_3$ receptor agonists (e.g. pumosetrag), 5-HT$_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic M$_1$ and M$_2$ antagonists (e.g. acotiamide), motilin agonists (e.g. mitemcinal), guanylate cyclase activators (e.g. MD-1100) and ghrelin agonists (e.g. Tzp 101, RC 1139).

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 μg/day to about 100 mg/day.

Accordingly, the pharmaceutical compositions of the invention optionally include a second therapeutic agent as described above.

The following examples illustrate representative pharmaceutical compositions of the present invention:

Formulation Example A

Hard Gelatin Capsules for Oral Administration

A compound of the invention (50 g), spray-dried lactose (200 g) and magnesium stearate (10 g) are thoroughly blended. The resulting composition is loaded into a hard gelatin capsule (260 mg of composition per capsule).

Formulation Example B

Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

Formulation Example C

Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

Formulation Example D

Tablets for Oral Administration

A compound of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

Formulation Example E

Tablets for Oral Administration

A compound of the invention (25 mg), microcrystalline cellulose (400 mg), fumed silicon dioxide (10 mg), and stearic acid (5 mg) are thoroughly blended and then compressed to form tablets (440 mg of composition per tablet).

Formulation Example F

Single-Scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

Formulation Example G

Suspension for Oral Administration

The following ingredients are thoroughly mixed to form a suspension for oral administration containing 100 mg of active ingredient per 10 mL of suspension:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Formulation Example H

Dry Powder Composition

A micronized compound of the invention (1 mg) is blended with lactose (25 mg) and then loaded into a gelatin inhalation cartridge. The contents of the cartridge are administered using a powder inhaler.

Formulation Example J

Injectable Formulation

A compound of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

Formulation Example K

Single-Scored Tablets for Oral Administration

A compound of the invention (10 mg), oxycodone hydrochloride (10 mg), cornstarch (50 mg), croscarmellose sodium (25 mg), lactose (120 mg), and magnesium stearate (5 mg) are thoroughly blended and then compressed to form single-scored tablet (220 mg of compositions per tablet).

Formulation Example L

Injectable Formulation

A compound of the invention (0.1 g) and oxycodone hydrochloride (0.1 g) are blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of the compounds of the invention, (i.e. free base, pharmaceutical salt, or solvate) that is suitable for the particular mode of administration, can be used in the pharmaceutical compositions discussed above.

Utility

The 3-carboxypropyl-aminotetralin compounds of the invention are antagonists at the mu opioid receptor and therefore are expected to be useful for treating medical conditions mediated by mu opioid receptors or associated with mu opioid receptor activity, i.e. medical conditions which are ameliorated by treatment with a mu opioid receptor antagonist. In particular, the compounds of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The mu opioid receptor antagonists of the invention are also expected to be useful for treating post-operative ileus, a disorder of reduced motility of the gastrointestinal tract that occurs after abdominal or other surgery. In addition, it has been suggested that mu opioid receptor antagonist compounds may be used for reversing opioid-induced nausea and vomiting. Further, those mu opioid receptor antagonists exhibiting some central penetration may be useful in the treatment of dependency on, or addiction to, narcotic drugs, alcohol, or gambling, or in preventing, treating, and/or ameliorating obesity.

Since compounds of the invention increase motility of the gastrointestinal (GI) tract in animal models, the compounds are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by mu opioid receptors, the compounds of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

As described above, compounds of the invention are mu opioid receptor antagonists. The invention further provides, therefore, a method of antagonizing a mu opioid receptor in a mammal, the method comprising administering a compound of the invention to the mammal.

The mu opioid receptor antagonists of the invention are optionally administered in combination with another therapeutic agent or agents, in particular, in combination with opioid analgesics or with prokinetic agents acting via non-mu opioid mechanisms. Accordingly, in another aspect, the methods and compositions of the invention further comprise a therapeutically effective amount of an opioid analgesic or another prokinetic agent. The methods of the invention include, for example, a method of reducing or preventing a side effect associated with use of an opioid agent in a mammal, the method comprising administering to the mammal an opioid agent and a compound of the invention.

In addition, the compounds of the invention are also useful as research tools for investigating or studying biological systems or samples having mu opioid receptors, or for discovering new compounds having mu opioid receptor activity. Any suitable biological system or sample having mu opioid receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of contacting a biological system or sample comprising a mu opioid receptor with a compound of the invention are determined using conventional procedures and equipment, such as the radioligand binding assay and functional assay described herein or other functional assays known in the art. Such functional assays include, but are not limited to, ligand-mediated changes in intracellular cyclic adenosine monophosphate (cAMP), ligand-mediated changes in activity of the enzyme adenylyl cyclase, ligand-mediated changes in incorporation of analogs of guanosine triphosphate (GTP), such as [$^{35}$S] GTPγS (guanosine 5'-O-(γ-thio)triphosphate) or GTP-Eu, into isolated membranes via receptor catalyzed exchange of GTP analogs for GDP analogs, and ligand-mediated changes in free intracellular calcium ions. A suitable concentration of a compound of the invention for such studies typically ranges from about 1 nanomolar to about 500 nanomolar.

When using compounds of the invention as research tools for discovering new compounds have mu opioid receptor activity, binding or functional data for a test compound or a group of test compounds is compared to the mu opioid receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to exhibit potent binding to mu opioid receptors and little or no agonism in mu receptor functional assays. Therefore, the compounds of the invention are potent mu opioid receptor antagonists. Further, compounds of the invention have demonstrated predominantly peripheral activity as compared with central nervous system activity in animal models. Therefore, these compounds can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings
ACN=acetonitrile
AcOH=acetic acid
Boc=tert-butoxycarbonyl
(Boc)$_2$O=di-tert-butyl dicarbonate
DCM=dichloromethane
DIPEA=N,N-diisopropylethylamine
DMF=N,N-dimethylformamide
DMSO=dimethyl sulfoxide
EtOAc=ethyl acetate
EtOH=ethanol
HATU=N,N,N',N'-tetramethyl-O-(7-azabenzotriazol-1-yl)uronium hexafluorophosphate
MeOH=methanol
MeTHF=2-methyl-tetrahydrofuran
MTBE=methyl tert-butyl ether
RT=room temperature
TFA=trifluoroacetic acid
THF=tetrahydrofuran Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

Preparation 1: 7,7-diethyl-5-hydroxy-1a,2,7,7a-tetrahydro-1-aza-cyclopropa[b]naphthalene-1-carboxylic acid tert-butyl ester a. 7-Amino-6-bromo-8,8-diethyl-5,6,7,8-tetrahydronaphthalen-2-ol hydrobromide To a flask was added 7,7-diethyl-5-methoxy-1a,2,7,7a-tetrahydro-1H-1-aza-cyclopropa[b]naphthalene (268 g, 1.16 mol) and hydrogen bromide (1.97 L, 17.38 mol), followed by tetra-N-butylammonium bromide (38 g, 0.12 mol). The reaction mixture was heated at 100° C. overnight with stirring, cooled to room temperature and then poured into stirred ethyl acetate (2.5 L). The product was isolated by filtration, the filter cake was washed with ethyl acetate (2×200 mL) and dried to yield crude product (370 g) as a purplish solid. The crude product was suspended in ethanol (1.50 L) then heated at 80° C. for 30 min. The resulting slurry was cooled to room temperature over 1 h, and filtered. The flask and filter cake with were washed with ethanol (2×100 mL) and then with ethyl acetate (100 mL) and dried overnight to yield the title compound as a solid. (275 g, ~96% purity).

b. 7,7-Di ethyl-5-hydroxy-1a,2,7,7a-tetrahydro-1-aza-cyclopropa[b]naphthalene-1-carboxylic acid tert-butyl ester To a slurry of 7-amino-6-bromo-8,8-diethyl-5,6,7,8-tetrahydronaphthalen-2-ol hydrobromide (20.0 g, 52.8 mmol) and ethyl acetate (200 mL) was added 1.0 M sodium hydroxide in water (106 mL). The reaction mixture was stirred at 25° C. for 2 h, di-tert-butyldicarbonate (15 g, 68 mmol) in ethyl acetate (5 mL) was added and the reaction mixture was stirred at room temperature for 2 h. Following removal of two-thirds of the ethyl acetate (135 mL), heptane (135 mL) was added and the resulting slurry was stirred at room temperature over 30 min and then at 5° C. overnight. The slurry was filtered, and the filter cake was rinsed with water (100 mL), rinsed with heptane (50 mL), and dried under vacuum to give the title compound (14.3 g).

Preparation 2: trans-(7-Cyano-1,1-diethyl-3-methoxy-1,2,3,4-tetrahydro-naphthalen-2-yl)-carbamic acid tert-butyl ester a. trans-(1,1-Diethyl-7-hydroxy-3-methoxy-1,2,3,4-tetrahydro-naphthalen-2-yl)-carbamic acid tert-butyl ester To a slurry of 7,7-diethyl-5-hydroxy-1a,2,7,7a-tetrahydro-1-aza-cyclopropa[b]naphthalene-1-carboxylic acid tert-butyl ester (170.0 g, 535.6 mmol) and methanol (1700 mL) was added pyridinium p-toluenesulfonate (13.4 g, 53.6 mmol) and the reaction mixture was stirred at 40° C. for 4 h. The volume was reduced by rotary evaporation to ~300 mL resulting in a thick white slurry. The product was isolated by filtration; the filter cake was washed with cold methanol (50 mL) and dried in air for 3 h to yield the title compound (150 g). The filtrate was reduced to ~50 mL and stirred at 0° C. for 2 h, filtered, and dried to yield additional product (25 g).

b. trans-Trifluoro-methanesulfonic acid 7-tert-butoxycarbonylamino-8,8-diethyl-6-methoxy-5,6,7,8-tetrahydro-naphthalen-2-yl ester A mixture of trans-(1,1-diethyl-7-hydroxy-3-methoxy-1,2,3,4-tetrahydro-naphthalen-2-yl)-carbamic acid tert-butyl ester (195.0 g, 0.558 mol), triethylamine (160 mL, 1.1 mol) and ethyl acetate (2000 mL) was stirred at room temperature for 15 min and cooled to 0° C. followed by slow addition of trifluoro-methanesulfonyl chloride (150 g, 0.89 mol) keeping the internal temperature below 4° C. The resulting slurry was stirred at 0° C. for 1 h. Additional triethylamine (16 mL) followed by additional trifluoromethanesulfonyl chloride (15.0 g) was added slowly maintaining a temperature below 5° C. The reaction mixture was stirred at room temperature for an additional hour. Diluted brine (1.0 L) was added and the reaction mixture was stirred for 10 min at room temperature. The layers were separated; the organic layer was washed with diluted NaHCO$_3$ (1.0 L) and then concentrated to ~350 mL by rotary evaporation at 28° C. and stirred at room temperature for 30 min. Heptane (700 mL) was added and the resulting slurry was stirred at room temperature for 30 min, cooled to 4° C. and stirred for 1 h. The solids were filtered, washed with heptane, and then dried under vacuum to yield the title compound (193.0 g, >97% purity). The filtrate was concentrated, slurried in an isopropyl acetate and heptane mixture (1:3, 60 mL) over 30 min, filtered and dried to yield additional product (45.0 g, >97% purity).

c. trans-(7-Cyano-1,1-diethyl-3-methoxy-1,2,3,4-tetrahydro-naphthalen-2-yl)-carbamic acid tert-butyl ester Trifluoro-methanesulfonic acid 7-tert-butoxycarbonylamino-8,8-diethyl-6-methoxy-5,6,7,8-tetrahydro-naphthalen-2-yl ester (236.6 g, 0.49 mol) was dissolved in N,N-dimethylformamide (851 mL, 10.99 mol) and water (23.8 mL, 1.32 mol) at room temperature. The solution was purged with nitrogen for 5 min, and then connected to house vacuum for 5 min. Nitrogen purging and exposure to vacuum was repeated twice. To the reaction mixture was added zinc cyanide (34.2 g, 0.29 mol), tris(dibenzylideneacetone)dipalladium(0) (4.4 g, 4.8 mmol) and 1,1'-bis(diphenylphosphino) ferrocene (5.4 g, 9.7 mmol) with stirring. The reaction mixture was purged with nitrogen for 5 min, heated under nitrogen at 110° C. for 1 h, cooled to room temperature and then filtered through celite. The filtered reaction mixture was added slowly to water (3 L), cooled to 0° C. with stirring, stirred for 30 min at 0° C., and then filtered. The filter cake was washed with water (500 mL) and dried in air for 2 h, slurried in ethanol (1 L) with stirring over 1 h, and then filtered to give the title compound (165.0 g, >96% purity). The filtrate was dried (21.6 g) and dissolved in ethanol (110 mL) with stirring over 1 h, and the resulting slurry was filtered and dried under vacuum to give additional product (10.2 g, >98% purity).

Preparation 3: trans-(7-Carbamoyl-1,1-diethyl-3-methoxy-1,2,3,4-tetrahydro-naphthalen-2-yl)-carbamic acid tert-butyl ester A slurry of the product of Preparation 2 (160.0 g, 446.3 mmol) and methanol (3.3 L) was heated at 55° C. for 15 min, sodium perborate monohydrate (280 g, 2800 mmol) and water (330 mL) was added and the reaction mixture was heated at 55° C. overnight. Additional sodium perborate monohydrate (90 g) was added and the reaction mixture was heated at 55° C. overnight, then cooled to room temperature, and the inorganic solids were filtered off. The filtrate was transferred to a 5 L flask and most of the solvent was removed by rotary evaporation. To the resulting slurry was added water (1.1 L) and ethyl acetate (450 mL) and the reaction mixture was stirred at room temperature for 20 min. The reaction mixture was filtered and the filter cake was washed with water (200 mL) and then ethyl acetate (200 mL) and dried to yield the title compound (123 g, ~95% purity). The filtrate was concentrated to dryness and dried under vacuum to yield additional product (18 g, 65% purity).

Preparation 4: trans-(7-Carbamoyl-1,1-diethyl-3-methoxy-1,2,3,4-tetrahydro-naphthalen-2-yl)-carbamic acid tert-butyl ester To a mixture of trans-(7-cyano-1,1-diethyl-3-methoxy-1,2,3,4-tetrahydro-naphthalen-2-yl)-carbamic acid tert-butyl ester (33.0 g, 92 mmol), ethanol (45 mL), DMF (25 mL) and water (7.5 mL) was added hydrido(dimethylphosphoniousacid-kP) [hydrogen bis(dimethylphosphinito-kP)]platinum(II) (0.25 g, 0.58 mmol) and the reaction mixture was heated at 80° C. for 24 h. The reaction was cooled to room temperature and concentrated to dryness under vacuum to give the title compound (36.3 g) which was used without further purification. (m/z): [M+H]$^+$ calcd for $C_{21}H_{32}N_2O_4$ 377.24. found 377.8. $^1$H NMR (d$_6$-DMSO, 400 mHz) δ (ppm): 7.92 (s, 1H), 7.64 (m, 2H), 7.26 (s, 1H), 7.14 (d, J=7.9 Hz, 1H), 6.64 (d, J=9.4 Hz) 3.81 (t, J=10.0 Hz), 3.58 (m, 1H), 3.30 (s, 3H), 2.58 (dd, J=16.9 Hz, 9.4 Hz, 1H), 1.82 (m, 1H), 1.56-1.45 (m, 4H), 1.41 (s, 9H), 0.58 (m, 6H).

Preparation 5: trans-(7-Carbamoyl-1,1-diethyl-3-methoxy-1,2,3,4-tetrahydro-naphthalen-2-yl)-carbamic acid tert-butyl ester To a solution of trans-(7-cyano-1,1-diethyl-3-methoxy-1,2,3,4-tetrahydro-naphthalen-2-yl)-carbamic acid tert-butyl ester (8.5 g, 24 mmol) in DMSO (105 mL) was added K$_2$CO$_3$ (4.98 g, 36 mmol), and the mixture was stirred until all solids were dissolved. To the solution was added 30% hydrogen peroxide (12.2 mL, 120 mmol) in 0.5 mL portions over 45 min at a rate to keep the temperature 30-35° C. The reaction mixture was diluted with water (200 mL) and isopropyl acetate (500 mL), and sodium metabisulfite was added (10 g) to reduce excess peroxides. Layers were separated and the aqueous layer was extracted with isopropyl acetate (3×150 mL) and 10% MeOH/isopropyl acetate (2×100 mL). The combined organic layers were washed with water (3×150 mL) and saturated NaCl (100 mL), dried with $Na_2SO_4$ and concentrated to give the title compound (9.4 g). (m/z): [M+H] calcd for $C_{21}H_{32}N_2O_4$ 377.24. found 377.6.

Preparation 6: trans-7-Amino-8,8-diethyl-6-methoxy-5,6,7,8-tetrahydro-naphthalene-2-carboxylic acid amide Acetyl chloride (278.8 mL, 3920 mmol) was added dropwise to ethanol (382 mL, 6530 mmol) at −5° C. over 2 h keeping the internal temperature below 20° C. The resulting solution was added portion wise over 15 min, keeping the internal temperature below 30° C., to a slurry of trans-(7-carbamoyl-1,1-diethyl-3-methoxy-1,2,3,4-tetrahydro-naphthalen-2-yl)-carbamic acid tert-butyl ester (123.0 g, 327 mmol) and ethanol (500 mL) that had been cooled to 10° C. The reaction mixture was stirred at room temperature for 2 h, and concentrated to ~200 mL by rotary evaporation. Ethyl acetate (200 mL) was added and the resulting slurry was stirred at 0° C. for 30 min, filtered and dried to yield the hydrochloride salt of the title compound (102 g, >98% purity) as a white solid.

Preparation 7: Carbonic acid 4-nitro-phenyl ester (R)-1-phenyl-ethyl ester

A mixture of (R)-1-phenyl-ethanol (60.6 g, 0.496 mol), pyridine (42.5 mL, 0.526 mol) and 2-methyl-tetrahydrofuran (600 mL) was cooled to 0° C. and p-nitrophenyl chloroformate (100 g, 0.496 mol) was added over 15 min keeping the internal temperature below 5° C. The reaction mixture was warmed to room temperature and stirred for 2 h. To the reaction mixture was added 1.0 M HCl in water (300 mL). Layers were separated. The organic layer was washed with 1N HCl (300 mL) and brine (300 mL), filtered, concentrated to dryness by rotary evaporation, and dried under vacuum to give the title compound (140 g) as a clear yellow oil.

Preparation 8: (6S,7S)-7-Amino-8,8-diethyl-6-methoxy-5,6,7,8-tetrahydro-naphthalene-2-carboxylic acid amide a. ((2S,3S)-7-Carbamoyl-1,1-diethyl-3-methoxy-1,2,3,4-tetrahydro-naphthalen-2-yl)-carbamic acid (R)-1-phenyl-ethyl ester A mixture of carbonic acid 4-nitro-phenyl ester (R)-1-phenyl-ethyl ester (102 g, 357 mmol), N,N-dimethylformamide (200 mL) and triethylamine (32.7 mL, 235 mmol) was stirred at room temperature overnight. To the reaction mixture was added trans-7-amino-8,8-diethyl-6-methoxy-5,6,7,8-tetrahydro-naphthalene-2-carboxylic acid amide hydrochloride (100 g, 320 mmol), N,N-dimethylformamide (320 mL) and triethylamine (98.0 mL, 703 mmol). The reaction mixture was heated at 85° C. for 5 h and then stirred at room temperature overnight. Approximately 90% of the DMF was removed by distillation at 70° C. and the resulting thick oil was cooled to room temperature and then partitioned between ethyl acetate (1.5 L) and diluted brine (500 mL). The organic layer was washed with 1M NaOH (3×500 mL) and dried with $Na_2SO_4$. Most of the solvent was removed by rotary evaporation, 3 volumes ethyl acetate were added and resulting slurry was stirred at room temperature for 30 min, filtered and dried to give the title compound (48 g, >99% chemical and optical purity).

The filtrate was washed with 1M NaOH (200 mL) and then with diluted brine (2×200 mL). Most of the solvent was removed by rotary evaporation yielding a thick oil to which ethyl acetate (100 mL) was added. A pinch of seeds of the title compound was added and the reaction mixture was refrigerated at 0° C. after stirring for ~30 min. The resulting thin slurry was stirred for 5 min and filtered; flask and filter cake were washed with ethyl acetate (2×15 mL) to yield additional title compound (4.1 g, 97% chemical and >99% optical purity, 38% combined yield).

b. (6S,7S)-7-Amino-8,8-diethyl-6-methoxy-5,6,7,8-tetrahydro-naphthalene-2-carboxylic acid amide Acetyl chloride (193 mL, 2710 mmol) was added dropwise to ethanol (260 mL, 4500 mmol) at −5° C. over 40 min keeping the internal temperature below 30° C. The resulting solution was added over 5 min, at 10° C., to a mixture of ((2S,3S)-7-carbamoyl-1,1-diethyl-3-methoxy-1,2,3,4-tetrahydro-naphthalen-2-yl)-carbamic acid (R)-1-phenyl-ethyl ester (49.0 g, 115 mmol) and ethanol (200 mL). The reaction mixture was stirred at room temperature overnight, and concentrated to ~100 mL by rotary evaporation. Ethyl acetate (100 mL) was added and the resulting slurry was stirred at 0° C. for 30 min and filtered. The filter cake was washed with ethyl acetate and dried to yield the hydrochloride salt of the title compound (30 g, >99% purity). The volume of the filtrate was reduced almost to dryness. Isopropyl alcohol (20 mL) was added and the resulting thick slurry was stirred for 30 min and filtered. The filter cake was washed with ethyl acetate (2×20 mL) and dried under vacuum overnight to yield additional product (5.5 g, >97% purity). $^1$H NMR (DMSO-$d_6$): δ (ppm) 0.49 (t, 3H), 0.63 (t, 3H), 1.62 (q, 2H), 1.89 (m, 1H), 2.09 (m, 1H), 2.60 (dd, 1H), 3.22 (m, 1H), 3.41 (s, 3H), 3.50 (dd, 1H), 3.82 (q, 1H), 7.19 (d, 1H), 7.31 (br, 1H), 7.70 (d, 1H), 7.71 (s, 1H), 7.98 (br, 1H), 8.15 (br, 3H).

Preparation 9: trans-7-Amino-8,8-diethyl-6-methoxy-5,6,7,8-tetrahydro-naphthalen-2-ol To a solution of trans-(1,1-diethyl-7-hydroxy-3-methoxy-1,2,3,4-tetrahydro-naphthalen-2-yl)-carbamic acid tert-butyl ester (6.0 g, 17.2 mmol) in dichloromethane (60 mL) was added a solution of 4.0 N HCl in dioxane (21.5 mL, 86 mmol) over approximately 2 min. After stirring at room temperature overnight, the reaction mixture was concentrated at reduced pressure and dried under vacuum to give the hydrochloride salt of the title compound (5.5 g) (m/z): [M+H]$^+$ calcd for $C_{15}H_{23}NO_2$ 250.36. found 250.2. $^1$H NMR ($d_6$-DMSO, 400 mHz) δ (ppm) 9.26 (s, 1H), 8.09 (br s, 3H), 6.92 (d, J=8.0 Hz, 1H), 6.61 (m, 2H), 3.77 (m, 1H), 3.41 (s, 3H), 3.30 (dd, J=15.8 Hz, 5.9 Hz, 1H), 3.17 (m, 1H), 2.43 (dd, J=15.5 Hz, 9.6 Hz, 1H), 1.85 (m, 2H), 1.66-1.50 (m, 2H), 0.66 (t, J=7.4 Hz, 3H), 0.54 (t, J=7.1 Hz, 3H).

Preparation 10: (6S,7S)-7-Amino-8,8-diethyl-6-methoxy-5,6,7,8-tetrahydro-naphthalen-2-ol and (6R,7R)-7-Amino-8,8-diethyl-6-methoxy-5,6,7,8-tetrahydro-naphthalen-2-ol a. ((2R,3R)-1,1-Diethyl-7-hydroxy-3-methoxy-1,2,3,4-tetrahydro-naphthalen-2-yl)-carbamic acid (R)-1-phenyl-ethyl ester (RR) and ((2S,3S)-1,1-Diethyl-7-hydroxy-3-methoxy-1,2,3,4-tetrahydro-naphthalen-2-yl)-carbamic acid (R)-1-phenyl-ethyl ester (SS)

A mixture of trans-7-amino-8,8-diethyl-6-methoxy-5,6,7,8-tetrahydro-naphthalen-2-ol hydrochloride salt (1.00 g, 3.5 mmol), carbonic acid 4-nitro-phenyl ester (R)-1-phenyl-ethyl ester (800 mg, 2.8 mmol), triethylamine (707 mg, 7.0 mmol) and DMF (3.5 mL) was heated at 90° C. After 4 h, an additional portion of carbonic acid 4-nitro-phenyl ester (R)-1-phenyl-ethyl ester (200 mg, 0.7 mmol) was added, and heating continued for another 3 h. The reaction mixture was cooled and allowed to stand at room temperature overnight. The DMF was removed at reduced pressure and the residue was dissolved in ethyl acetate (25 mL). The organics were washed with 10% sodium carbonate and saturated sodium chloride, dried with $Na_2SO_4$ and concentrated to dryness. The residue was dissolved in methanol (6 mL) and a 1.0 N solution of sodium hydroxide in methanol (3.0 mL, 3.0 mmol) was added. The reaction mixture was stirred at room temperature for 30 min, at which time 50% aqueous acetic acid (2 mL) was added. The reaction mixture was concentrated to approximately 4 mL, and 50% aqueous acetonitrile (15 mL) was added.

The crude diastereomers were separated by preparative HPLC and collected separately. Crude product was dissolved in 1:1 acetonitrile/water and separated under the following conditions: column: Microsorb C18 100 A 8 μm column; flow rate: 50 mL/min; Solvent A: >99% water, 0.05 TFA; Solvent B: >99% acetonitrile, 0.05 TFA; Gradient (time(min)/% B): 0/15, 4/15, 8/40, 60/55. The pure fractions of each were pooled and the acetonitrile was removed at reduced pressure. The product was extracted into dichloromethane (3×30 mL), the organic extracts were dried with $Na_2SO_4$ and concentrated to give the title compounds.

RR: 435 mg (39% yield) (m/z): [M+H]$^+$ calcd for $C_{24}H_{31}NO_4$ 398.52. found 398.2. $^1$H NMR (d$_6$-DMSO, 400 mHz) δ (ppm) 9.01 (s, 1H), 7.37-7.26 (m, 5H), 7.05 (d, J=9.8 Hz, 1H), 6.86 (d, 8.2, 1H), 6.52 (dd, J=8.0, 2.4 Hz, 1H), 6.48 (d, J=2.3 Hz, 1H), 5.70 (guar, J=6.7 Hz, 1H), 3.77 (t, J=10.3 Hz, 1H), 3.55 (m, 1H), 3.32 (s, 3H), 3.17 (dd, J=15.9, 6.0 Hz, 1H), 2.43 (m, 1H), 1.57-1.52 (m, 2H), 1.56 (d, J=6.7 Hz, 3H), 1.44-1.33 (m, 2H), 0.60 (t, J=7.4 Hz, 3H), 0.51 (t, J=7.0 Hz, 3H).

SS: 363 mg (32% yield) (m/z): [M+H]$^+$ calcd for $C_{24}H_{31}NO_4$ 398.52. found 398.2. $^1$H NMR (d$_6$-DMSO, 400 mHz) δ (ppm) 9.02 (s, 1H), 7.39-7.24 (m, 5H), 7.03 (d, J=9.7 Hz, 1H), 6.85 (d, 8.3, 1H), 6.53 (dd, J=8.1, 2.6 Hz, 1H), 6.48 (d, J=2.2 Hz, 1H), 5.69 (guar, J=6.7 Hz, 1H), 3.75 (t, J=10.6 Hz, 1H), 3.52 (m, 1H), 3.27 (s, 3H), 3.14 (dd, J=15.9, 5.9 Hz, 1H), 2.37 (dd, J=15.7, 9.5, 1H), 1.65-1.41 (m, 4H), 1.46 (d, J=6.6 Hz, 3H), 0.64-0.60 m, 6H).

b. (6S,7S)-7-Amino-8,8-diethyl-6-methoxy-5,6,7,8-tetrahydro-naphthalen-2-ol ((2S,3S)-1,1-Diethyl-7-hydroxy-3-methoxy-1,2,3,4-tetrahydro-naphthalen-2-yl)-carbamic acid (R)-1-phenyl-ethyl ester (635 mg, 1.60 mmol) was treated with 4.0 N HCl in dioxane (6.0 mL, 24 mmol) and stirred at RT. After 3 days, the solvent was removed at reduced pressure and the residual solid was triturated with 50% dichloromethane in heptane (4 mL). The solid was collected on a Buchner funnel and dried under vacuum to give the hydrochloride salt of the title compound (462 mg). (m/z): [M+H]$^+$ calcd for $C_{15}H_{23}NO_2$ 250.36. found 250.2. $^1$H NMR (d$_6$-DMSO, 400 mHz) δ (ppm) 9.23 (s, 1H), 8.02 (br s, 3H), 6.92 (d, J=8.2 Hz, 1H), 6.61 (m, 2H), 3.77 (m, 1H), 3.41 (s, 3H), 3.30 (m, 1H), 3.17 (m, 1H), 2.44 (dd, J=15.9 Hz, 9.8 Hz, 1H), 1.85 (m, 2H), 1.62-1.52 (m, 2H), 0.66 (t, J=7.2 Hz, 3H), 0.55 (t, J=7.0 Hz, 3H).

c. (6R,7R)-7-Amino-8,8-diethyl-6-methoxy-5,6,7,8-tetrahydro-naphthalen-2-ol

Following the procedure of the previous step using ((2R,3R)-1,1-diethyl-7-hydroxy-3-methoxy-1,2,3,4-tetrahydro-naphthalen-2-yl)-carbamic acid (R)-1-phenyl-ethyl ester, the hydrochloride salt of the title compound was prepared. (m/z): [M+H]$^+$ calcd for $C_{15}H_{23}NO_2$ 250.36. found 250.4. $^1$H NMR (d$_6$-DMSO, 400 mHz) δ (ppm) 9.23 (s, 1H), 8.02 (br s, 3H), 6.92 (d, J=8.2 Hz, 1H), 6.61 (m, 2H), 3.77 (m, 1H), 3.41 (s, 3H), 3.30 (m, 1H), 3.17 (m, 1H), 2.44 (dd, J=15.7 Hz, 10.2 Hz, 1H), 1.84 (m, 2H), 1.62-1.52 (m, 2H), 0.66 (t, J=7.4 Hz, 3H), 0.55 (t, J=7.0 Hz, 3H).

Preparation 11: ((2S,3S)-7-Carbamoyl-1,1-diethyl-3-methoxy-1,2,3,4-tetrahydro-naphthalen-2-yl)-carbamic acid (R)-1-phenyl-ethyl ester (SS) and ((2R,3R)-7-Carbamoyl-1,1-diethyl-3-methoxy-1,2,3,4-tetrahydro-naphthalen-2-yl)-carbamic acid (R)-1-phenyl-ethyl ester (RR)

A mixture of carbonic acid 4-nitro-phenyl ester (R)-1-phenyl-ethyl ester (7.35 g, 25.6 mol), trans-7-amino-8,8-diethyl-6-methoxy-5,6,7,8-tetrahydro-naphthalene-2-carboxylic acid amide hydrochloride (4.0 g, 13 mmol) and triethylamine (5.3 mL, 38 mol) in DMF (13 mL) was heated at 85° C. After 2.5 hours, the reaction mixture was cooled and stirred at room temperature overnight. Solvent was removed under vacuum and the residue was purified by silica gel chromatography eluting with EtOAc in DCM (10% to 50% gradient) to give a mixture containing the title compounds (6.96 g). The mixture of diastereomers was separated by preparative HPLC under the conditions described in Preparation 10 (a) except for use of the following gradient (time (min)/% B): 0/5, 4/5, 8/37, 60/42. The pure fractions of each isomer were pooled and lyophylized to give the title compounds.

SS: 1.4 g (26%) (m/z): [M+H]$^+$ calcd for $C_{25}H_{32}N_2O_4$ 425.24. found 425.6.

RR: 1.5 g (28%) (m/z): [M+H]$^+$ calcd for $C_{25}H_{32}N_2O_4$ 425.24. found 425.4.

Single Crystal X-Ray Diffraction Analysis of Diastereomer SS

SS (3 mg) was dissolved in acetonitrile (100 mL) in an open HPLC vial, which was partially immersed in a 20 mL vial containing 1:9 acetonitrile:water (4 mL). The 20 mL vial was capped and held at room temperature to provide large birefringent needle shaped crystals of SS.

X-ray diffraction crystal structure data was obtained for a single crystal with dimensions 0.44×0.13×0.10 mm using Mo K$_α$ radiation (λ=0.71073 Å) on a Nonius KappaCCD diffractometer equipped with a graphite crystal and incident beam monochromator, and analyzed on a LINUX PC using SHELX97 software. The following lattice parameters were derived: unit cell is hexagonal with dimensions a=17.451 Å, b=17.451 Å, c=19.822 Å, α=90.00°, β=90.00°, γ=120.00°, cell volume (V)=5228 Å³, space group is P 3₁21. The molecule contains three chiral centers. From the known R configuration of the carbon bearing the phenyl group:

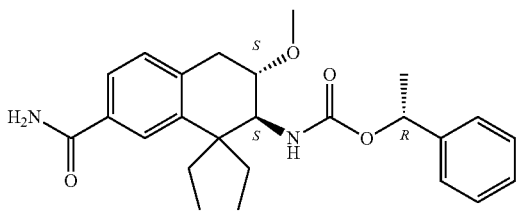

the remaining two centers were determined to be in the S configuration.

Remaining crystals were analyzed by powder x-ray diffraction. Powder x-ray diffraction peaks predicted from the derived single crystal crystallographic data were in good agreement with observed powder x-ray diffraction peaks.

Preparation 12: (6R,7R)-7-Amino-8,8-diethyl-6-methoxy-5,6,7,8-tetrahydro-naphthalene-2-carboxylic acid amide ((2R,3R)-7-Carbamoyl-1,1-diethyl-3-methoxy-1,2,3,4-tetrahydro-naphthalen-2-yl)-carbamic acid (R)-1-phenyl-ethyl ester (1.7 g, 4.0 mmol) was treated with 4.0 N HCl in dioxane (20 mL, 80 mmol) and stirred at RT. After 24 h, the solvent was removed at reduced pressure and the residual solid was triturated with 50% dichloromethane in hexane (15 mL). The solid was collected on a Buchner funnel, rinsed with 50% dichloromethane in hexane (10 mL) and dried under vacuum to give the title compound as the hydrochloride salt (1.2 g). (m/z): [M+H]⁺ calcd for $C_{16}H_{24}N_2O_2$ 277.19. found 277.4. ¹H NMR (d₆-DMSO, 400 mHz) δ (ppm) 8.19 (br s, 3H), 7.98 (s, 1H), 7.70 (m, 2H), 7.32 (s, 1H) 7.19 (d, J=7.8 Hz, 1H), 3.83 (m, 1H), 3.47 (m, 1H), 3.42 (s, 3H), 3.23 (m, 1H), 2.63 (dd, J=16.8 Hz, 9.7 Hz, 1H) 2.06 (m, 1H), 1.88 (m, 1H) 1.64 (guar, J=7.7 Hz, 2H), 0.62 (t, J=7.5 Hz, 3H), 0.50 (t, J=7.0 Hz, 3H).

Preparation 13: Sodium (S)-4-cyclohexyl-1-hydroxy-3-methoxycarbonyl-butane-1-sulfonate a: (S)-2-Cyclohexylmethyl-4-hydroxy-butyric acid methyl ester A mixture of (S)-2-cyclohexylmethyl-succinic acid 1-methyl ester (60.0 g, 263 mmol) and tetrahydrofuran (600 mL) was stirred at room temperature and then cooled to −5° C. over 30 min. To the reaction mixture was added 1.0 M borane in tetrahydrofuran (520 mL) dropwise over 45 min, keeping the internal temperature below 0° C. To the reaction mixture was added MeOH (100 mL) dropwise to quench the reaction. The reaction mixture was concentrated to about 100 mL by rotary evaporation. (Trifluoromethyl)benzene (200 mL) was added and volume was reduced to 25 mL by rotary evaporation. (Trifluoromethyl)benzene (100 mL) was added to the resulting thick oil and the volume was reduced to ~25 mL to provide crude title product (56.3 g).

b. Sodium (S)-4-cyclohexyl-1-hydroxy-3-methoxycarbonyl-butane-1-sulfonate

A mixture of (S)-2-cyclohexylmethyl-4-hydroxy-butyric acid methyl ester (44.8 g, 209 mmol) and DCM (310 mL) was cooled to 5° C. with stirring. To the reaction mixture was added a solution of potassium bromide (2.5 g, 21 mmol) and sodium bicarbonate (2.4 g, 29 mmol) in distilled water (130 mL), and then 2,2,6,6-tetramethylpiperidin-1-oxyl (TEMPO) (0.33 g, 2.1 mmol), followed by the addition of sodium hypochlorite (140 mL, 210 mmol) at the rate of 130 mL/h keeping the internal temperature in the range of 6-8° C. The reaction mixture was stirred for 15 min and DCM (200 mL) was added. Layers were separated and the organic layer was washed with saturated brine (200 mL), and dried with $Na_2SO_4$.

To the organic layer was added EtOAc (40 mL) followed by the addition of sodium bisulfite (21.8 g, 209 mmol). The reaction solution was concentrated to remove half of the DCM (~175 mL) by rotary evaporation. Water (2 mL) were added to the reaction solution which was stirred at room temperature overnight. The resulting slurry was filtered; the filter cake was dried under vacuum overnight to yield the title compound (61.9 g). ¹H NMR (DMSO-d₆): δ (ppm) 0.78 (m, 2H), 0.95-1.20 (m, 4H), 1.33 (m, 1H), 1.40-1.95 (m, 5H), 2.45-2.65 (m, 1H), 3.21 (m, 2H), 3.45 (s, 3H), 3.6-3.8 (m, 1H), 5.18 (d, 1H).

Preparation 14: trans-7-Amino-8,8-dimethyl-6-methoxy-5,6,7,8-tetrahydro-naphthalene-2-carboxylic acid amide a. 7-Methoxy-1,1-dimethyl-3,4-dihydro-1H-naphtalen-2-one A slurry of sodium tent butoxide (21.1 g, 220 mmol) in THF (100 mL) was cooled to 0° C. A solution of 7-methoxy-3,4-dihydro-1H-napthalen-2-one (17.6 g, 100 mmol) and methyl iodide (30.1 g, 220 mmol) in THF (100 mL) was added dropwise over 40 min, and the reaction mixture was warmed to room temperature after 10 min. Water (200 mL) and EtOAc (600 mL) was added. The layers were separated, the organic layer was washed with water (5×100 mL) and saturated NaCl (100 mL), filtered and dried with $Na_2SO_4$ to provide the title compound (20 g).

b. 7-Methoxy-1,1-dimethyl-3,4-dihydro-1H-naptha-len-2-one oxime

To a solution of 7-methoxy-1,1-dimethyl-3,4-dihydro-1H-napthalen-2-one (25.4 g, 98 mmol) in methanol (175 mL) was added a solution of hydroxylamine hydrochloride (20.5 g, 295 mmol) and sodium acetate (24.2 g, 295 mmol) in water (175 mL) and the reaction mixture was heated at 70° C. for 3 h, and cooled in ice over 30 min. The solid was collected on a Buchner funnel, stirred with methanol (125 mL) at 50° C. for 30 min, and then stirred at RT overnight. The reaction mixture was cooled to 0° C.; solid was collected on a Buchner funnel, rinsed with cold methanol (20 mL) and dried under vacuum to give the title compound (14.7 g).

c. (1aS,7aR)-4-Methoxy-2,2-dimethyl-1a,2,7,7a-tetrahydro-1H-1-aza-cyclopropa[b]-naphthalene To a solution of 7-methoxy-1,1-dimethyl-3,4-dihydro-1H-napthalen-2-one (15.3 g, 70 mmol) in THF (240 mL) was added diethylamine (18 mL). The reaction mixture was cooled to 0° C. and a 2.0 M solution of lithium aluminum hydride in THF (100 mL, 200 mmol) was added slowly over 20 min to control the rate of hydrogen evolution. The reaction mixture was heated to 70° C. for 1 h, cooled to 0° C. and $Na_2SO_4$ 10$H_2O$ (20 g), brine (60 mL), and EtOAc (300 mL)

were added. The solid were washed with EtOAc (4×100 mL); the combined organic layers were washed with water (4×100 mL) and brine (100 mL), dried with $Na_2SO_4$, and concentrated to give crude title product (14.3 g). The crude product was dissolved in EtOAc (500 mL), extracted with 0.1 N HCl (100 mL), then with 0.3 N HCl (225 mL). Sodium carbonate (8 g, 75 mmol) was added to the aqueous layer which was extracted with EtOAc (4×200 mL). Organic layers were combined, dried with $Na_2SO_4$ and concentrated to give the title compound as an oil (10.1 g) which crystallized on standing to a tan solid. (m/z): [M+H] calcd for $C_{11}H_{17}NO$ 204.14. found 204.2.

d. trans-(7-Hydroxy-3-methoxy-1,1-dimethyl-1,2,3,4-tetrahydro-naphthalen-2-yl)-carbamic acid tert-butyl ester Using a procedure similar to that of Preparations 1(b) and 2(a), the title compound was prepared. $^1$H NMR ($d_6$-DMSO, 400 mHz) δ (ppm): 9.04 (s, 1H), 6.83 (d, J=8.2 Hz, 1H), 6.69 (d, J=9.4 Hz, 1H), 6.65 (d, J=2.5 Hz, 1H), 6.52 (dd, J=8.2, 2.5 Hz, 1H), 3.50 (m, 1H), 3.45 (m, 1H), 3.30 (s, 3H), 3.15 (m, 1H), 2.55 (m, 1H), 1.34 (s, 9H), 1.16 (s, 3H), 1.00 (s, 3H).

e. trans-(7-Carbamoyl-3-methoxy-1,1-dimethyl-1,2,3,4-tetrahydro-naphthalen-2-yl)-carbamic acid tert-butyl ester Using a procedure similar to that of Preparations 2(b), 2(c), and 5, the title compound was prepared. (m/z): [M+H]$^+$ calcd for $C_{19}H_{28}N_2O_4$ 349.21. found 349.1.

f. trans-(7-Amino-6-methoxy-8,8-dimethyl-5,6,7,8-tetrahydronaphthalene-2-carboxylic acid amide To a slurry of trans-(7-carbamoyl-3-methoxy-1,1-dimethyl-1,2,3,4-tetrahydro-naphthalen-2-yl)-carbamic acid tert-butyl ester (9.22 g, 26.4 mmol) in DCM (100 mL) was added 4 N HCl in dioxane (25 mL, 100 mmol) slowly. The reaction mixture was stirred at RT for 15 h, concentrated to dryness, triturated with DCM (25 mL) for 30 min, filtered, rinsed with DCM (3×15 mL), and dried under vacuum. Ethanol (100 mL) was added and the reaction mixture was concentrated under vacuum to give the HCl salt of the title compound (7.17 g) as a white powder. (m/z): [M+H] calcd for $C_{14}H_{20}N_2O_2$ 249.16. found 249.1. $^1$H NMR ($d_6$-DMSO, 400 mHz) δ (ppm): 8.18 (s, 3H), 8.00 (s, 1H), 7.92 (d, J=1.6 Hz, 1H), 7.66 (dd, J=8.0 Hz, 1.8 Hz, 1H), 7.32 (s, 1H), 7.17 (d, J=8.0 Hz, 1H), 3.70 (m, 1H), 3.44 (s, 3H), 3.43 (m, 1H), 3.22 (m, 1H), 2.67 (dd, J=16.4 Hz, 10.2 Hz, 1H), 1.50 (s, 3H), 1.24 (s, 3H).

Preparation 15: (S)-2-Cyclohexylmethyl-4-oxo-butyric acid methyl ester a. (S)-2-Cyclohexylmethyl-4-hydroxy-butyric acid methyl ester

A mixture of (S)-2-cyclohexylmethyl-succinic acid 1-methyl ester (484 mg, 2.12 mmol) and tetrahydrofuran 10 mL) was stirred at room temperature and then cooled to 0° C. To the reaction mixture was added 1.0 M borane in tetrahydrofuran (4.2 mL) dropwise over 5 min. After 2 h, MeOH was added drop-wise to quench the reaction. The reaction mixture was stirred for 30 min at room temperature and then concentrated to dryness. The crude residue was suspended in MeOH, concentrated to dryness, and purified on $SiO_2$ (40 g) using 5-10% MeOH/DCM as eluent to provide the title compound (0.32 g) as a clear oil: $^1$H NMR ($CDCl_3$, 400 mHz) δ (ppm): 3.69-3.65 (m, 5H), 2.65 (m, 1H), 1.85-1.59 (m, 8H), 1.32-1.12 (m, 5H), 0.87 (m, 2H).

b. (S)-2-Cyclohexylmethyl-4-oxo-butyric acid methyl ester

A mixture of the product of the previous step (0.32 g, 1.49 mmol), N,N-diisopropylethylamine (0.65 mL, 3.7 mmol), dimethyl sulfoxide (0.26 mL, 3.7 mmol), and dichloromethane (20 mL, 0.3 mol) was cooled to 0° C. and flushed with nitrogen. Sulfur trioxide-pyridine complex (0.59 g, 3.7 mmol) was added under a stream of nitrogen and the reaction mixture was stirred for 1.5 h. To the reaction mixture was added 0.1 N HCl. The organic layer was washed with 0.1N HCl (2×) and brine (2×), dried with $Na_2SO_4$, filtered, and concentrated to dryness to provide the title compound (0.305 g) as a clear oil which was used without further purification. $^1$H NMR ($CDCl_3$, 400 mHz) δ (ppm): 9.75 (s, 1H), 3.69 (s, 3H), 3.02-2.96 (m, 1H), 2.84 (dd, J=18.0, 9.0 Hz, 1H), 2.55 (dd, J=18, 4.7 Hz, 1H), 1.79-1.12 (m, 11H), 0.93-0.84 (m, 2H).

Preparation 16: Aldehyde Reagents

Following the process of Preparation 14 using the appropriate methyl ester in place of (S)-2-cyclohexylmethyl-succinic acid 1-methyl ester, the following aldehydes were prepared:

(R)-2-Cyclohexylmethyl-4-oxo-butyric acid methyl ester: $^1$H NMR ($CDCl_3$, 400 mHz) δ (ppm): 9.76 (s, 1H), 3.69 (s, 3H), 3.01-2.96 (m, 1H), 2.84 (dd, J=18.0, 9.0 Hz, 1H), 2.55 (dd, J=18, 4.7 Hz, 1H), 1.79-1.14 (m, 11H), 0.92-0.96 (m, 2H).

(S)-2-Cyclohexyl-4-oxo-butyric acid methyl ester: $^1$H NMR ($CDCl_3$, 400 mHz) δ(ppm): 9.78 (s, 1H), 3.69 (s, 3H), 2.91 (dd, J=18, 10 Hz, 1H), 2.80-2.75 (m, 1H), 2.56 (dd, J=18, 3.5 Hz, 1H), 1.84-0.98 (m, 11H).

(S)-2-pentyl-4-oxo-butyric acid methyl ester: $^1$H NMR ($CDCl_3$, 400 mHz) δ(ppm): 9.76 (s, 1H), 3.70 (s, 3H), 2.92-2.84 (m, 2H), 2.80-2.75 (m, 1H), 2.58-2.54 (m, 1H), 1.67-1.63 (m, 1H), 1.57-1.48 (m, 2H), 1.28 (bs, 6H), 0.89-0.86 (m, 3H).

(S)-2-Phenylpropyl-4-oxo-butyric acid methyl ester: $^1$H NMR ($CDCl_3$, 400 mHz): confirmed the presence of aldehyde with a peak at 9.75 (s, 1H).

(S)-2-Isobutyl-4-oxo-butyric acid methyl ester: $^1$H NMR ($CDCl_3$, 400 mHz) δ(ppm): 9.76 (s, 1H), 3.70 (s, 3H), 3.1-2.94 (m, 1H), 2.88-2.81 (m, 1H), 2.62-2.52 (m, 1H), 1.66-1.26 (m, 3H), 0.97-0.88 (m, 6H).

(R)-2-Isobutyl-4-oxo-butyric acid methyl ester: $^1$H NMR ($CDCl_3$, 400 mHz) δ(ppm): 9.76 (s, 1H), 3.70 (s, 3H), 2.96-2.93 (m, 1H), 2.84 (dd, J=18, 9.0 Hz, 1H), 2.55 (dd, J=18, 4.5 Hz, 1H), 1.64-1.25 (m, 3H), 0.94-0.86 (m, 6H).

(S)-2-Isopropyl-4-oxo-butyric acid methyl ester. $^1$H NMR ($CDCl_3$, 400 mHz): confirmed the presence of aldehyde with a peak at 9.79 (s, 1H).

(S)-4,4-Dimethyl-2-(2-oxo-ethyl)-pentanoic acid methyl ester: $^1$H NMR ($CDCl_3$, 400 mHz) δ (ppm): 9.73 (s, 1H), 3.69 (s, 3H), 2.80 (dd, J=17.8, 8.0 Hz, 1H), 2.57 (dd, J=18, 5.8 Hz, 1H), 1.79 (dd, J=14, 8.41 Hz, 1H), 1.50-1.40 (m, 1H), 1.25 (dd, J=14, 3.7 Hz, 1H), 0.91 (s, 9H).

(R)-4,4-Dimethyl-2-(2-oxo-ethyl)-pentanoic acid methyl ester: $^1$H NMR ($CDCl_3$, 400 mHz) δ (ppm): 9.73 (s, 1H), 3.69 (s, 3H), 2.80 (dd, J=17.8, 8.0 Hz, 1H), 2.57 (dd, J=17.8, 5.67

Hz, 1H), 1.79 (dd, J=14.1, 8.41 Hz, 1H), 1.50-1.41 (m, 1H), 1.25 (dd, J=14.1, 3.7 Hz, 1H), 0.91 (s, 9H).

(S)-Benzyl-4-oxo-butyric acid methyl ester: $^1$H NMR (CDCl$_3$, 400 mHz) δ (ppm): confirmed the presence of aldehyde with a peak at 9.70 (s, 1H)

(R)-2-Butyl-4-oxo-butyric acid methyl ester: $^1$H NMR (CDCl$_3$, 400 mHz) δ (ppm): 9.76 (s, 1H), 3.69 (s, 3H), 2.91-2.87 (m, 1H), 2.57-2.54 (m, 1H), 1.70-1.25 (m, 6H), 0.92-0.87 (m, 3H)

Preparation 17: Sodium (S)-3-benzyloxycarbonyl-4-cyclohexyl-1-hydroxy-butane-1-sulfonate a. (S)-2-cyclohexylmethyl-4,4-dimethoxy-butyric acid methyl ester To a slurry of sodium (S)-4-cyclohexyl-1-hydroxy-3-methoxycarbonyl-butane-1-sulfonate (400.0 g, 1.26 mol) and methanol (2 L) was added 4.0 M HCl in 1,4-dioxane (400 mL) and the reaction mixture was stirred for 15 min. Trimethoxymethane (340 mL, 3.11 mol) was added and reaction mixture was heated at 50° C. overnight, and then cooled to room temperature. White solids were filtered off and discarded. Most of the solvent was removed from the filtrate by rotary evaporation. Ethyl acetate (800 mL) was added resulting in more precipitation. The white precipitate was removed by filtration. Solvent was removed from the filtrate by rotary evaporation and then under high vacuum at room temperature overnight to yield the title compound (211 g) as a thick oil. $^1$H NMR (400 MHz, DMSO-d$_6$): δ (ppm) 4.25 (t, 1H), 3.57 (s, 3H), 3.18 (s, 6H), 2.43 (m, 1H), 1.55-1.81 (m, 2H), 1.50-1.72 (m, 5H), 1.20-1.48 (m, 2H), 1.05-1.21 (m, 4H), 0.71-0.92 (m, 2H).

b. Potassium (S)-2-cyclohexylmethyl-4,4-dimethoxy-butyrate

Potassium hydroxide (289.6 g, 2322 mmol) was added to a solution of the product of the previous step (200.0 g, 0.77 mol) in methanol (700 mL) in one portion and the reaction mixture was stirred at RT for 20 h. Hydrogen chloride (130 mL, 1.5 mol) was added slowly until the reaction mixture had a pH ~8 (color change from greenish to orange) resulting in precipitation of fine solids. Solids were removed by filtration. Solvent was removed from the filtrate. Acetonitrile (1 L) was added to the crude product and the resulting slurry was stirred at room temperature overnight. The thick slurry was filtered, the filter cake was washed with acetonitrile (50 mL) and dried to yield a first crop of the title compound (133 g) as an off-white solid. Solvent was removed from the filtrate which was then dried under vacuum to yield about 100 g of a pasty solid. MTBE (500 mL) was added and the solids were stirred at RT overnight resulting in a thick slurry which was filtered and dried under high vacuum to yield a second crop of the title compound (82 g). $^1$H NMR (400 MHz, DMSO-d$_6$): δ (ppm) 4.28 (dd, 1H), 3.12 (s, 3H), 3.15 (s, 3H), 1.95 (m, 1H), 1.75 (m, 1H), 1.51-1.65 (m, 6H), 1.22-1.39 (m, 2H), 1.05-1.20 (m, 4H), 0.85-0.93 (m, 1H), 0.65-0.81 (m, 2H).

c: (S)-2-Cyclohexylmethyl-4,4-dimethoxy-butyric acid benzyl ester

Benzyl bromide (50.54 mL, 424.9 mmol) was added to a slurry of the product of the previous step (150.0 g, 531.1 mmol) in acetonitrile (2.0 L) in one portion and the heterogeneous reaction mixture was stirred at room temperature overnight. Additional benzyl bromide (5.05 mL, 42.49 mmol) was added and the reaction mixture was stirred at room temperature for 18 h. Solids were removed by filtration. The filtrate was dried by rotary evaporation and then under high vacuum overnight yielding the title compound (162 g). $^1$H NMR (400 MHz, DMSO-d$_6$): δ 7.22-7.40 (m, 5H), 5.0-5.15 (q, 2H), 4.23 (t, 1H), 3.15 (s, 3H), 3.17 (s, 3H), 2.52 (m, 1H), 1.78 (m, 1H), 1.69 (m, 1H), 1.45-1.61 (m, 6H), 1.20-1.43 (m, 2H), 1.0-1.15 (m, 4H), 0.70-0.83 (m, 2H).

d. Sodium (S)-3-benzyloxycarbonyl-4-cyclohexyl-1-hydroxy-butane-1-sulfonate

To a mixture of the product of the previous step (160.0 g, 478.4 mmol) and acetonitrile (1.0 L) was added 1.0 M HCl in water (1.2 L) and the reaction mixture was heated at 35-40° C. for 2 h. Ethyl acetate (1.2 L) was added, phases were separated, and the organic layer was washed with brine (1 L). Sodium bisulfite (74.7 g, 718 mmol) was added to the wet organic layer and the reaction mixture was stirred at RT overnight. Most of the solvent was removed by rotary evaporation and acetonitrile (1 L) was added and the resulting slurry was stirred at RT overnight. The resulting thick white slurry was filtered, the filter cake was washed with acetonitrile (2×100 mL) and dried under vacuum to yield the title compound (200 g, >98% purity) as a white solid. $^1$H NMR (400 MHz, DMSO-d$_6$): δ 7.23-7.41 (m, 5H), 5.30 (d, 1H), 4.98-5.18 (q, 2H), 3.75-3.88 (m, 1H), 3.60-3.79 (m, 1H), 2.05 (m, 0.5H), 1.45-1.82 (m, 2.5H), 1.45-1.60 (m, 5H), 1.20-1.42 (m, 2H), 1.0-1.17 (m, 4H), 0.69-0.82 (m, 2H).

Example 1

(S)-4-((2S,3S)-7-Carbamoyl-1,1-diethyl-3-methoxy-1,2,3,4-tetrahydro-naphthalen-2-ylamino)-2-cyclohexylmethyl-butyric acid a. (S)-4-((2S,3S)-7-Carbamoyl-1,1-diethyl-3-methoxy-1,2,3,4-tetrahydro-naphthalen-2-ylamino)-2-cyclohexylmethyl-butyric acid methyl ester To a slurry of sodium (S)-4-cyclohexyl-1-hydroxy-3-methoxycarbonyl-butane-1-sulfonate (25.8 g, 81.5 mmol) and 2-methyl-tetrahydro-furan (300 mL) was added 1.0 M NaOH in water (76.1 mL) and the reaction mixture was stirred for 20 min at RT. To the reaction mixture was added (6S,7S)-7-Amino-8,8-diethyl-6-methoxy-5,6,7,8-tetrahydro-naphthalene-2-carboxylic acid amide hydrochloride (17.0 g, 54.3 mmol); the reaction mixture was stirred for 40 min at RT, sodium triacetoxyborohydride (46.1 g, 217 mmol) was added in 4 portions. The reaction mixture was stirred at RT overnight after the first two portions. Water (200 mL) and MeTHF (100 mL) were added; the phases were separated and the organic layer was washed with 1 M NaOH (2×200 mL), diluted brine (200 mL) dried with Na$_2$SO$_4$ and solvent was removed to yield crude title intermediate (22 g) as a glassy yellow solid.

Crude product was purified by reverse-phase chromatography using a Microsorb 100-10 BDS 4 inch column. Crude product was dissolved in 1:1 acetonitrile: 1 M aq. HCl (150 mL) solvent mixture and eluted with water (0.1% HCl)/acetonitrile mobile phase (10-40% gradient). Pure fractions (>98%) were combined, most of the acetonitrile was removed by rotary evaporation, pH was adjusted to pH ~12 with solid Na$_2$CO$_3$ and purified product was extracted with MeTHF (3×1 L). Combined organic layers were dried with Na$_2$SO$_4$ and solvent removed to yield the title compound (16.5 g)

b. (S)-4-((2S,3S)-7-Carbamoyl-1,1-diethyl-3-methoxy-1,2,3,4-tetrahydro-naphthalen-2-ylamino)-2-cyclohexylmethyl-butyric acid To a solution of (S)-4-((2S,3S)-7-carbamoyl-1,1-diethyl-3-methoxy-1,2,3,4-tetrahydro-naphthalen-2-ylamino)-2-cyclohexylmethyl-butyric acid methyl ester (12.0 g, 25.4 mmol) in methanol was added 5.0 M NaOH (25 mL) and the reaction mixture was heated at 30° C. for 8 h and then at 25° C. overnight. Most of the methanol solvent was removed by rotary evaporation at 25° C., water (100 mL) and isopropyl acetate (100 mL) was added and the resulting mixture was stirred for 15 min. The bottom two of three layers were extracted with isopropyl acetate (100 mL). Bottom layers were cooled to −5° C. and MeTHF (200 mL) was added and then concentrated HCl (~15 mL) was added in portions until pH ~2. Phases were separated, water layer was washed with MeTHF (100 mL) and combined organic layers were dried with $Na_2SO_4$. Most of the organic solvent was removed by rotary evaporation, ethyl acetate (200 mL) was added and the volume was reduced to 50 mL. Ethyl acetate (200 mL) was added and the resulting slurry was stirred/triturated at RT for 3 h. Product was filtered under nitrogen and dried under vacuum for 48 h to yield the hydrochloride salt of the title compound (11 g, 98.2% purity) as a white solid. $^1$H NMR (DMSO-$d_6$): δ (ppm) 0.54 (t, 3H), 0.63 (t, 3H), 0.82 (m, 2H), 1.05-1.3 (m, 6H), 1.45 (m, 1H), 1.55-2.0 (m, 10H), 2.40 (m, 1H), 2.67 (dd, 1H), 3.06 (m, 1H), 3.22 (m, 1H), 3.30 (dd, 1H), 3.41 (s, 3H), 3.45 (dd, 1H), 4.05 (m, 1H), 7.19 (d, 1H), 7.50 (br, 1H), 7.69 (d, 1h), 7.70 (s, 1H), 7.95 (br, 2H), 9.26 (br, 1H).

Example 2

(S)-4-((2S,3S)-7-Carbamoyl-1,1-diethyl-3-methoxy-1,2,3,4-tetrahydro-naphthalen-2-ylamino)-2-cyclohexylmethyl-butyric acid methyl ester (S)-2-cyclohexylmethyl-4-oxo-butyric acid methyl ester (822 mg, 3.38 mmol), (6S,7S)-7-amino-8,8-diethyl-6-methoxy-5,6,7,8-tetrahydronaphthalene-2-carboxylic acid amide hydrochloride (1.01 g, 3.23 mmol) and triethylamine (326 mg, 3.23 mmol) were dissolved in dichloromethane (15 mL) and methanol (10 mL). Sodium triacetoxyborohydride (1.03 g, 4.85 mmol) was added. Over 3 h, additional sodium triacetoxyborohydride (900 mg, 4.2 mol) and (S)-2-cyclohexylmethyl-4-oxo-butyric acid methyl ester (550 mg, 2.6 mmol) were added in two portions, and the reaction mixture was stirred for 1 h after the last addition. Saturated sodium bicarbonate (60 mL) was added, and the reaction mixture was extracted with dichloromethane (4×50 mL). The organic layer was dried with $Na_2SO_4$ and concentrated. The resulting oil was dissolved in methanol (50 mL) and concentrated. The crude product was purified by preparative HPLC. Fractions containing pure product were pooled and the acetonitrile was removed at reduced pressure. Sodium carbonate (1.3 g, 12.3 mmol) was added and the product extracted into dichloromethane (3×200 mL). An additional portion of sodium sulfate (15 g, 140 mmol) was added to the aqueous layer which was extracted with dichloromethane (3×200 mL). The organic extracts were combined, dried with $Na_2SO_4$ and concentrated to give the title compound as the free base (1.16 g, 76% yield).

(m/z): $[M+H]^+$ calcd for $C_{28}H_{44}N_2O_4$, 473.67. found, 473.4. $^1$H NMR (CDCl$_3$, 400 mHz) δ (ppm): 7.66 (d, J=1.8 Hz, 1H), 7.50 (dd, J=8.0 Hz, 1.9 Hz, 1H), 7.13 (d, J=8.0 Hz, 1H), 3.65 (s, 3H), 3.58 (m, 1H), 3.47 (s, 3H), 3.31 (dd, J=16.7, 6.1 Hz, 1H), 2.97 (m, 1H), 2.74-2.64 (m, 3H), 2.57 (m, 1H), 1.90-1.53 (m, 14H), 1.33-1.11 (m, 6H), 0.89-0.83 (m, 3H), 0.69 (t, J=7.6 Hz, 3H), 0.59 (t, J=7.3 Hz, 3H).

Example 3

(S)-4-((2S,3S)-7-Carbamoyl-1,1-diethyl-3-methoxy-1,2,3,4-tetrahydro-naphthalen-2-ylamino)-2-cyclohexylmethyl-butyric acid A mixture of the product of Example 2 (685 mg, 1.43 mmol), 10 N NaOH (0.87 mL, 8.7 mmol), methanol (4.5 mL) and water (0.45 mL) was heated at 55° C. for 2 h. The mixture was cooled to room temperature, diluted with 50% aqueous acetic acid and purified by preparative HPLC. Clean fractions were combined with those from another run (0.79 mmol scale) and lyophilized to give the title compound (1.02 g, 80% yield) as the TFA salt. (m/z): $[M+H]^+$ calcd for $C_{27}H_{42}N_2O_4$, 459.32. found, 459.8. $^1$H NMR ($d_6$-DMSO, 400 mHz) δ (ppm): 8.92 (br s, 1H), 7.97 (s, 1H), 7.70 (m, 3H), 7.35 (s, 1H), 7.22 (d, J=8.4 Hz, 1H), 4.01 (m, 1H), 3.48 (dd, J=16.4, 5.7 Hz, 1H), 3.42 (s, 3H), 3.36 (m, 1H), 3.27 (m, 1H), 3.10 (m, 1H), 2.70 (dd, J=16.8, 10.2 Hz, 1H), 2.43 (m, 1H), 2.15 (m, 1H), 1.90 (m, 2H), 1.69-1.59 (m, 8H), 1.49 (m, 1H), 1.28-1.09 (m, 5H) 0.86, (m, 2H), 0.66 (t, J=7.4 Hz, 3H), 0.58 (t, J=7.0 Hz, 3H).

Example 4

(S)-4-(2R,3R)-7-Carbamoyl-1,1-diethyl-3-methoxy-1,2,3,4-tetrahydro-naphthalen-2-ylamino)-2-cyclohexylmethyl-butyric acid methyl ester Following the procedure of Example 2 using (6R,7R)-7-amino-8,8-diethyl-6-methoxy-5,6,7,8-tetrahydronaphthalene-2-carboxylic acid amide hydrochloride gave the title compound. (m/z): $[M+H]^+$ calcd for $C_{28}H_{44}N_2O_4$, 473.34. found, 473.4.

Example 5

(R)-4-((2R,3R)-7-Carbamoyl-1,1-diethyl-3-methoxy-1,2,3,4-tetrahydro-naphthalen-2-ylamino)-2-cyclohexylmethyl-butyric acid methyl ester (6R,7R)-7-Amino-8,8-diethyl-6-methoxy-5,6,7,8-tetrahydro-naphthalene-2-carboxylic acid amide hydrochloride (0.16 g, 0.51 mmol) was dissolved in dichloromethane (4.4 mL) and methanol (2 mL) at room temperature. (R)-2-Cyclohexylmethyl-4-oxo-butyric acid methyl ester (0.22 g, 1.0 mmol) was added followed by triethylamine (0.071 mL, 0.51 mmol) and sodium triacetoxyborohydride (0.16 g, 0.77 mmol). Over the course of 2 h, additional sodium triacetoxyborohydride (0.16 g) was added. Saturated sodium bicarbonate was added and the reaction mixture was extracted with DCM. The organic extract was washed with brine (2×), dried over sodium sulfate, filtered, and concentrated to dryness. The crude product was dissolved in 1:1 AcOH/H$_2$O and was purified by preparative HPLC to give the title compound as the TFA salt (161 mg, 53.6% yield). (m/z): $[M+H]^+$ calcd for $C_{28}H_{44}N_2O_4$, 473.33. found, 473.4. $^1$H NMR (DMSO-$d_6$, 400 mHz) δ (ppm): 8.92 (bs, 1H), 7.95 (s, 1H), 7.70 (s, 2H), 7.68 (s, 1H), 7.33 (s, 1H), 7.20 (d, J=8.4 Hz, 1H), 4.02-3.96 (m, 1H), 3.61 (s, 1H), 3.46 (dd, J=16.8, 5.87 Hz, 1H), 3.40 (s, 3H), 3.35-3.31 (m, 1H), 3.20-3.08 (m, 2H), 2.68 (dd, J=16.4, 9.78 Hz, 1H), 2.51-2.58 (m, 1H), 2.16-2.11 (m, 1H), 1.96-

1.86 (m, 2H), 1.77-1.59 (m, 9H), 1.50-1.44 (m, 1H), 1.16-1.10 (s, 4H), 0.88-0.83 (m, 2H), 0.64 (t, J=7.4 Hz, 3H), 0.56 (t, J=7.4 Hz, 3H).

Example 6

(R)-4-((2S,3SR)-7-Carbamoyl-1,1-diethyl-3-methoxy-1,2,3,4-tetrahydro-naphthalen-2-ylamino)-2-cyclohexylmethyl-butyric acid methyl ester Following the procedure of Example 5 using (6S,7S)-7-Amino-8,8-diethyl-6-methoxy-5,6,7,8-tetrahydro-naphthalene-2-carboxylic acid amide hydrochloride the title compound was prepared. (m/z): [M+H] calcd for $C_{28}H_{44}N_2O_4$, 473.33. found, 473.4. $^1$H NMR (DMSO-$d_6$, 400 mHz) δ (ppm): 8.90 (bs, 1H), 7.96 (s, 1H), 7.74 (bs, 1H), 7.70 (s, 1H), 7.68 (s, 1H), 7.32 (s, 1H), 7.20 (d, J=8.4 Hz, 1H), 4.04-4.97 (m, 1H), 3.60 (s, 1H), 3.47 (dd, J=16.8, 5.67 Hz, 1H), 3.40 (s, 3H), 3.33-3.22 (m, 2H), 3.03 (m, 1H), 2.69-2.57 (m, 2H), 2.17-2.11 (m, 1H), 1.99-1.96 (m, 1H), 1.86-1.59 (m, 9H), 1.50-1.43 (m, 1H), 1.32-1.25 (m, 1H), 1.17-1.06 (s, 4H), 0.89-0.80 (m, 2H), 0.64 (t, J=7.4 Hz, 3H), 0.56 (t, J=7.4 Hz, 3H).

Example 7

(S)-2-[2-((2S,3S)-7-Carbamoyl-1,1-diethyl-3-methoxy-1,2,3,4-tetrahydro-naphthalen-2-ylamino)-ethyl]-4-methyl-pentanoic acid methyl ester (7-A) and (S)-2-[2-((2S,3S)-7-Carbamoyl-1,1-diethyl-3-methoxy-1,2,3,4-tetrahydro-naphthalen-2-ylamino)-ethyl]-4-methyl-pentanoic acid (7-B)

(6S,7S)-7-Amino-8,8-diethyl-6-methoxy-5,6,7,8-tetrahydro-naphthalene-2-carboxylic acid amide hydrochloride (0.19 g; 0.62 mmol) was dissolved in (3 mL) and methanol (1.85 mL) at room temperature. (S)-2-Isobutyl-4-oxo-butyric acid methyl ester (0.212 g, 1.23 mmol) was added followed by triethylamine (0.086 mL, 0.62 mmol), and then sodium triacetoxyborohydride (0.20 g, 0.92 mmol). Over the course of 3 h, additional (S)-2-isobutyl-4-oxo-butyric acid methyl ester (0.070 g) and sodium triacetoxyborohydride (0.15 g) were added. Saturated sodium bicarbonate was added and the reaction mixture was extracted with DCM. The organic extract was dried with sodium sulfate, filtered, and concentrated to dryness. The crude residue was dissolved in methanol (3 mL) and 5 N NaOH (0.15 mL). The reaction mixture was heated at 50° C. for 17 h then cooled to room temperature, diluted with 1:1 AcOH/$H_2O$ (3 mL), and purified by preparative HPLC to give the TFA salts of the title compounds.

7-A: (35.3 mg, 10.2% yield over 2 steps). (m/z): [M+H]$^+$ calcd for $C_{25}H_{40}N_2O_4$, 433.30. found, 433.4. $^1$H NMR (DMSO-$d_6$, 400 mHz) δ (ppm): 8.94 (bs, 1H), 7.95 (s, 1H), 7.69 (s, 2H), 7.68 (s, 1H), 7.29 (s, 1H), 7.16 (d, J=8.6 Hz, 1H), 4.01 (m, 1H), 3.61 (s, 3H), 3.46 (dd, J=16.6, 5.67 Hz, 1H), 3.40 (s, 3H), 3.35-3.30 (m, 1H), 3.12-3.09 (m, 2H), 2.67 (dd, J=16.4, 9.78 Hz, 1H), 2.5 (m, 1H), 2.16-2.10 (m, 1H), 1.92-1.87 (m, 2H), 1.78-1.59 (m, 3H), 1.52-1.45 (m, 2H), 1.29-1.22 (m, 1H), 0.85 (t, J=6.7, 6H), 0.63 (t, J=7.4 Hz, 3H), 0.56 (t, J=7.4 Hz, 3H).

7-B: (30 mg, 8.8% over 2 steps). (m/z): [M+H]$^+$ calcd for $C_{24}H_{38}N_2O_4$, 419.28; found, 419.6. $^1$H NMR (DMSO-$d_6$, 400 mHz) δ (ppm): 12.42 (bs, 1H), 8.89 (bs, 1H), 7.95 (s, 1H), 7.70 (s, 2H), 7.68 (s, 1H), 7.33 (s, 1H), 7.19 (d, J=8.6 Hz, 1H), 4.0 (m, 1H), 3.49-3.47 (m, 1H), 3.40 (s, 3H), 3.36-3.30 (m, 1H), 3.24 (bs, 1H), 3.1 (m, 1H), 2.65 (dd, J=16.4, 9.78 Hz, 1H), 2.42-2.41 (m, 1H), 2.16-2.10 (m, 1H), 1.94-1.81 (m, 2H), 1.80-1.42 (m, 6H), 1.27-1.21 (m, 1H), 0.93-0.80 (m, 8H), 0.64 (t, J=7.4 Hz, 3H), 0.56 (t, J=7.4 Hz, 3H).

Example 8

Following the procedure of Example 7 using the appropriate methyl ester in place of (S)-2-isobutyl-4-oxo-butyric acid methyl ester, TFA salts of the following compounds were prepared:

8-A: (R)-2-[2-((2S,3S)-7-Carbamoyl-1,1-diethyl-3-methoxy-1,2,3,4-tetrahydro-naphthalen-2-ylamino)-ethyl]-4-methyl-pentanoic acid methyl ester: (m/z): [M+H]$^1$ calcd for $C_{25}H_{40}N_2O_4$, 433.30. found, 433.6. $^1$H NMR (DMSO-$d_6$, 400 mHz) δ (ppm): 8.84 (bs, 1H), 7.93 (s, 1H), 7.68 (s, 2H), 7.66 (s, 1H), 7.31 (s, 1H), 7.18 (d, J=8.6 Hz, 1H), 3.98 (m, 1H), 3.59 (s, 3H), 3.46 (dd, J=16.6, 5.28 Hz, 1H), 3.38 (s, 3H), 3.32-3.23 (m, 2H), 3.02 (bs, 1H), 2.63 (dd, J=16.2, 9.4 Hz, 1H), 2.55 (m, 1H), 2.16-2.10 (m, 1H), 1.97-1.95 (m, 1H), 1.83-1.59 (m, 3H), 1.49-1.43 (m, 2H), 1.26-1.23 (m, 1H), 0.84 (t, J=6.1 Hz, 6H), 0.63 (t, J=7.4 Hz, 3H), 0.54 (t, J=7.4 Hz, 3H).

8-B: (R)-2-[2-((2S,3S)-7-Carbamoyl-1,1-diethyl-3-methoxy-1,2,3,4-tetrahydro-naphthalen-2-ylamino)-ethyl]-4-methyl-pentanoic acid: (m/z): [M+H]$^+$ calcd for $C_{24}H_{38}N_2O_4$, 419.28. found, 419.4. $^1$H NMR (DMSO-$d_6$, 400 mHz) δ (ppm): 12.41 (bs, 1H), 8.88 (bs, 1H), 7.93 (s, 1H), 7.68 (s, 2H), 7.66 (s, 1H), 7.31 (s, 1H), 7.18 (d, J=8.4 Hz, 1H), 4.01-3.94 (m, 1H), 3.46 (dd, J=16.6, 16.6 Hz, 1H), 3.38 (s, 3H), 3.32-3.26 (m, 1H), 3.04 (bs, 1H), 2.65 (dd, J=16.6, 9.79 Hz, 1H), 2.42-2.37 (m, 1H), 2.15-2.02 (m, 1H), 1.95-1.92 (m, 1H), 1.81-1.42 (m, 6H), 1.24-1.17 (m, 1H), 0.85 (t, J=6.2 Hz, 6H), 0.63 (t, J=7.4 Hz, 3H), 0.54 (t, J=7.4 Hz, 3H).

8-C: (R)-2-[2-((2S,3S)-7-Carbamoyl-1,1-diethyl-3-methoxy-1,2,3,4-tetrahydro-naphthalen-2-ylamino)-ethyl]-3-methyl-butyric acid methyl ester: (m/z): [M+H]$^+$ calcd for $C_{24}H_{38}N_2O_4$, 419.28. found, 419.4.

8-D: (R)-2-[2-((2S,3S)-7-Carbamoyl-1,1-diethyl-3-methoxy-1,2,3,4-tetrahydro-naphthalen-2-ylamino)-ethyl]-3-methyl-butyric acid: (m/z): [M+H]$^+$ calcd for $C_{23}H_{36}N_2O_4$, 405.27. found, 405.4. $^1$H NMR (DMSO-$d_6$, 400 mHz) δ (ppm): 112.39 (bs, 1H), 8.92 (bs, 1H), 7.94 (s, 1H), 7.68 (s, 2H), 7.67 (s, 1H), 7.32 (s, 1H), 7.19 (d, J=8.4 Hz, 1H), 4.01-3.96 (m, 1H), 3.46 (dd, J=16.6, 5.68 Hz, 1H), 3.39 (s, 3H), 3.34-3.31 (m, 1H), 3.25 (bs, 1H), 3.04 (bs, 1H), 2.64 (dd, J=16.4, 9.59 Hz, 1H), 2.23-2.09 (m, 2H), 1.98-1.59 (m, 6H), 0.89-0.86 (m, 4H), 0.63 (t, J=7.4 Hz, 3H), 0.55 (t, J=7.4 Hz, 3H).

8-E: (R)-2-[2-((2S,3S)-7-Carbamoyl-1,1-diethyl-3-methoxy-1,2,3,4-tetrahydro-naphthalen-2-ylamino)-ethyl]-4,4-dimethyl-pentanoic acid methyl ester: (m/z): [M+H]$^+$ calcd for $C_{26}H_{42}N_2O_4$, 447.31. found, 447.6.

8-F: (R)-2-[2-((2S,3S)-7-Carbamoyl-1,1-diethyl-3-methoxy-1,2,3,4-tetrahydro-naphthalen-2-ylamino)-ethyl]-4,4-dimethyl-pentanoic acid: (m/z): [M+H]$^+$ calcd for $C_{25}H_{40}N_2O_4$, 433.30. found, 433.2. $^1$H NMR (DMSO-$d_6$, 400 mHz) δ (ppm): 8.90 (bs, 1H), 7.94 (s, 1H), 7.69 (s, 2H), 7.67 (s, 1H), 7.32 (s, 1H), 7.19 (d, J=8.4 Hz, 1H), 4.01-3.94 (m, 1H), 3.46 (dd, J=17.0, 5.87 Hz, 1H), 3.39 (s, 3H), 3.33-3.27 (m, 1H), 3.25 (bs, 1H), 3.03 (bs, 1H), 2.64 (dd, J=16.4, 9.78 Hz, 1H), 2.31-2.35 (m, H), 2.16-2.10 (m, 1H), 1.97-1.94 (m, 1H), 1.80-1.57 (m, 5H), 1.18 (dd, J=13.8, 2.93 Hz, 1H), 0.85 (m, 9H), 0.65 (t, J=7.4 Hz, 3H), 0.54 (t, J=7.4 Hz, 3H).

Example 9

(S)-2-[2-((2S,3S)-7-Carbamoyl-1,1-diethyl-3-methoxy-1,2,3,4-tetrahydro-naphthalen-2-ylamino)-ethyl]-heptanoic acid (6S,7S)-7-Amino-8,8-diethyl-6-methoxy-5,6,7,8-tetrahydro-naphthalene-2-carboxylic acid amide hydrochloride (0.20 g; 0.64 mmol) was dissolved in dichloromethane (3 mL) and methanol (1.92 mL) at room temperature. (S)-2-Pentyl-4-oxo-butyric acid methyl ester (0.24 g, 1.3 mmol) was added followed by triethylamine (0.089 mL, 0.64 mmol) and sodium triacetoxyborohydride (0.20 g, 0.96 mmol). Over the course of 90 min, additional sodium triacetoxyborohydride (0.070 g, 0.33 mmol) was added. Saturated sodium bicarbonate was added and the reaction mixture was extracted with DCM. The organic layer was dried with sodium sulfate, filtered, and concentrated to dryness (0.40 g). The crude residue was dissolved in MeOH (3 mL) and 5 N NaOH (0.40 mL) was added. The reaction mixture was heated at 50° C. for 5 h, then cooled at room temperature while stirring overnight. The crude reaction mixture was diluted with 1:1 AcOH/H$_2$O (3 mL) and purified by preparative HPLC to give the title compound as the TFA salt (32 mg, 8.8% over 2 steps). (m/z): [M+H]$^+$ calcd for C$_{25}$H$_{40}$N$_2$O$_4$, 433.30; found, 433.4. $^1$H NMR (DMSO-d$_6$, 400 mHz) δ (ppm): 7.91 (s, 1H), 7.66 (s, 2H), 7.64 (s, 1H), 7.29 (s, 1H), 7.16 (d, J=8.6 Hz, 1H), 3.97-3.91 (m, 1H), 3.43 (dd, J=16.4, 5.48 Hz, 1H), 3.36 (s, 3H), 3.31-3.17 (m, 2H), 3.02 (m, 1H), 2.63 (dd, J=16.4, 9.78 Hz, 1H), 2.34-2.26 (m, 1H), 2.12-2.00 (m, 1H), 1.88-1.82 (m, 2H), 1.74-1.51 (m, 3H), 1.49-1.36 (m, 2H), 1.20 (s, 6H), 0.80 (t, J=6.7, 4H), 0.60 (t, J=7.4 Hz, 3H), 0.52 (t, J=7.4 Hz, 3H).

Example 10

Following the procedure of Example 9 using the appropriate methyl ester in place of (S)-2-pentyl-4-oxo-butyric acid methyl ester, TFA salts of the following compounds were prepared:

10-A: (S)-2-[2-((2S,3S)-7-Carbamoyl-1,1-diethyl-3-methoxy-1,2,3,4-tetrahydro-naphthalen-2-ylamino)-ethyl]-5-phenyl-pentanoic acid: (m/z): [M+H]$^+$ calcd for C$_{29}$H$_{40}$N$_2$O$_4$, 481.30. found, 481.4. $^1$H NMR (DMSO-d$_6$, 400 mHz) δ (ppm): 12.39 (bs, 1H), 8.87 (bs, 1H), 7.92 (s, 1H), 7.65 (m, 3H), 7.29 (s, 1H), 7.22-7.05 (m, 7H), 3.98-3.91 (m, 1H), 3.43 (dd, J=16.6, 5.67 Hz, 1H), 3.35 (s, 3H), 3.31-3.17 (m, 2H), 3.04 (bs, 1H), 2.63 (dd, J=16.6, 9.59 Hz, 1H), 2.52 (t, J=6.6 Hz, 2H), 2.34 (m, 1H), 2.12-2.06 (m, 1H), 1.88-1.82 (m, 2H), 1.74-1.41 (m, 7H), 1.49-1.36 (m, 2H), 1.20 (s, 6H), 0.80 (t, J=6.7, 3H), 0.60 (t, J=7.4 Hz, 3H), 0.514 (t, J=7.4 Hz, 3H).

10-B: (S)-2-[2-((2S,3S)-7-Carbamoyl-1,1-diethyl-3-methoxy-1,2,3,4-tetrahydro-naphthalen-2-ylamino)-ethyl]-4,4-dimethyl-pentanoic acid: (m/z): [M+H]$^+$ calcd for C$_{25}$H$_{40}$N$_2$O$_4$, 433.30. found, 433.6. $^1$H NMR (DMSO-d$_6$, 400 mHz) δ (ppm): 12.39 (bs, 1H), 8.87 (bs, 1H), 7.93 (s, 1H), 7.66 (s, 2H), 7.64 (s, 1H), 7.31 (s, 1H), 7.18 (d, J=8.2 Hz, 1H), 3.96 (m, 1H), 3.43 (dd, J=16.8, 5.87 Hz, 1H), 3.38 (s, 3H), 3.29 (bs, 1H), 3.18-3.10 (m, 1H), 2.66 (dd, J=16.4, 9.97 Hz, 1H), 2.32 (m, 1H), 2.14-2.08 (m, 1H), 1.87 (m, 2H), 1.76-1.58 (m, 4H), 1.18 (m, 1H), 0.84 (s, 9H), 0.62 (t, J=7.4 Hz, 3H), 0.54 (t, J=7.4 Hz, 3H).

10-C: (S)-2-Benzyl-4-((2S,3S)-7-carbamoyl-1,1-diethyl-3-methoxy-1,2,3,4-tetrahydro-naphthalen-2-ylamino)-butyric acid: (m/z): [M+H]$^+$ calcd for C$_{27}$H$_{36}$N$_2$O$_4$, 453.27. found, 453.1. $^1$H NMR (DMSO-d$_6$, 400 mHz) δ (ppm): 8.86 (bs, 1H), 7.93 (s, 1H), 7.68 (s, 1H), 7.67 (s, 2H), 7.31-7.16 (m, 5H), 7.17 (d, J=8.2 Hz, 1H), 4.0-3.93 (m, 1H), 3.46 (dd, J=16.8, 5.87 Hz, 1H), 3.38 (s, 3H), 3.35-3.26 (m, 2H), 3.04 (bs, 1H), 2.91-2.86 (m, 1H), 2.76-2.61 (m, 2H), 2.17-2.07 (m, 1H), 1.89-1.83 (m, 2H), 1.72-1.55 (m, 3H), 0.61 (t, J=7.4 Hz, 3H), 0.51 (t, J=7.4 Hz, 3H).

10-D: (R)-2-[2-((2S,3S)-7-Carbamoyl-1,1-diethyl-3-methoxy-1,2,3,4-tetrahydro-naphthalen-2-ylamino)-ethyl]-hexanoic acid: (m/z): [M+H]$^+$ calcd for C$_{27}$H$_{36}$N$_2$O$_4$, 419.28. found, 419.3. $^1$H NMR (DMSO-d$_6$, 400 mHz) δ (ppm): 7.97 (s, 1H), 7.72 (s, 2H), 7.70 (s, 1H), 7.34 (s, 1H), 7.22 (d, J=8.1 Hz, 1H), 4.04-3.98 (m, 1H), 3.48 (dd, J=16.8, 5.68 Hz, 1H), 3.42 (s, 3H), 3.37-3.25 (m, 2H), 3.09-3.05 (m, 1H), 2.68 (dd, J=16.6, 9.78 Hz, 1H), 2.44-2.40 (m, 1H), 2.29-2.13 (m, 1H), 2.01-1.98 (m, 1H), 1.86-1.62 (m, 4H), 1.55-1.46 (m, 2H), 1.34-1.22 (m, 6H), 0.87 (t, J=6.8, 4H), 0.66 (t, J=7.4 Hz, 3H), 0.58 (t, J=7.4 Hz, 3H).

10-E: (S)-4-((2R,3R)-7-Carbamoyl-1,1-diethyl-3-methoxy-1,2,3,4-tetrahydro-naphthalen-2-ylamino)-2-cyclohexylmethyl-butyric acid: (m/z): [M+H]$^+$ calcd for C$_{27}$H$_{42}$N$_2$O$_4$, 459.31. found, 459.4. $^1$H NMR (DMSO-d$_6$, 400 mHz) δ (ppm): 12.42 (bs, 1H), 8.84 (bs, 1H), 7.95 (s, 1H), 7.69-7.65 (m, 3H), 7.33 (s, 1H), 7.20 (d, J=8.6 Hz, 1H), 4.04-3.96 (m, 1H), 3.47 (dd, J=16.8, 5.86 Hz, 1H), 3.40 (s, 3H), 3.35-3.22 (m, 2H), 3.06 (bs, 1H), 2.66 (dd, J=16.4, 9.39 Hz, 1H), 2.32 (m, 1H), 2.17-2.12 (m, 1H), 1.96-1.90 (m, 1H), 1.81-1.60 (m, 9H), 1.50-1.44 (m, 1H), 1.29-1.07 (m, 5H), 0.91-0.81 (m, 2H), 0.64 (t, J=7.4 Hz, 3H), 0.55 (t, J=7.4 Hz, 3H).

10-F: (R)-4-((2R,3R)-7-Carbamoyl-1,1-diethyl-3-methoxy-1,2,3,4-tetrahydro-naphthalen-2-ylamino)-2-cyclohexylmethyl-butyric acid: m/z): [M+H]$^+$ calcd for C$_{27}$H$_{42}$N$_2$O$_4$, 459.31. found, 459.8.

10-G: (R)-4-((2S,3S)-7-Carbamoyl-1,1-diethyl-3-methoxy-1,2,3,4-tetrahydro-naphthalen-2-ylamino)-2-cyclohexylmethyl-butyric acid: (m/z): [M+H] calcd for C$_{27}$H$_{42}$N$_2$O$_4$, 459.31. found, 459.4. $^1$H NMR (DMSO-d$_6$, 400 mHz) δ (ppm): 12.4 (bs, 1H), 8.82 (bs, 1H), 7.91 (s, 1H), 7.66-7.61 (m, 3H), 7.29 (s, 1H), 7.16 (d, J=8.4 Hz, 1H), 4.06-3.93 (m, 1H), 3.43 (dd, J=17.2, 6.06 Hz, 1H), 3.36 (s, 3H), 3.31-3.25 (m, 2H), 3.0 (bs, 1H), 2.65-2.58 (m, 1H), 2.13-2.07 (m, 1H), 1.89 (m, 1H), 1.71-1.57 (m, 9H), 1.45-1.41 (m, 1H), 1.28-1.03 (m, 5H), 0.86-0.78 (m, 2H), 0.61 (t, J=7.4 Hz, 3H), 0.52 (t, J=7.4 Hz, 3H).

Example 11 trans-(S)-4-(7-Carbamoyl-3-methoxy-1,1-diethyl-1,2,3,4-tetrahydro-naphthalen-2-ylamino)-2-cyclohexyl-butyric acid Following the procedure of Example 9 using (S)-2-cyclohexyl-4-oxo-butyric acid methyl ester and the racemic compound trans-7-amino-8,8-diethyl-6-methoxy-5,6,7,8-tetrahydro-naphthalene-2-carboxylic acid amide hydrochloride, the TFA salt of the title compound was prepared. (m/z): [M+H]$^+$ calcd for C$_{26}$H$_{40}$N$_2$O$_4$, 445.30. found, 445.4

Example 12

(S)-2-Cyclohexylmethyl-4-((2S,3S)-1,1-diethyl-7-hydroxy-3-methoxy-1,2,3,4-tetrahydro-naphthalen-2-ylamino)-butyric acid a. (S)-2-Cyclohexylmethyl-4-((2S,3S)-1,1-diethyl-7-hydroxy-3-methoxy-1,2,3,4-tetrahydro-naphthalen-2-ylamino)-butyric acid methyl ester To a slurry of sodium (S)-4-cyclohexyl-1-hydroxy-3-methoxycarbonyl-butane-1-sulfonate (158 mg, 0.5 mmol) in 2-MeTHF (2 mL) was added 2N NaOH (0.22 mL, 0.44 mmol). The reaction mixture was stirred for 20 min at which time all of the solids had dissolved. (6S,7S)-7-Amino-8,8-diethyl-6-methoxy-5,6,7,8-tetrahydro-naphthalen-2-ol hydrochloride (100 mg, 0.35 mmol) was added and the mixture was stirred at RT for 30 min. Sodium triacetoxyborohydride (425 mg, 2.0 mmol) was added in 4 portions over 3 h. Thirty minutes after the last addition, EtOAc (15 mL) was added and the mixture was washed with 5% aqueous sodium carbonate (2×5 mL) and saturated sodium chloride (5 mL). The organic layer was dried with Na$_2$SO$_4$ and concentrated to give the title compound (159 mg). (m/z): [M+H]$^+$ calcd for C$_{27}$H$_{43}$NO$_4$, 446.33. found, 446.6.

b. (S)-2-Cyclohexylmethyl-4-((2S,3S)-1,1-diethyl-7-hydroxy-3-methoxy-1,2,3,4-tetrahydro-naphthalen-2-ylamino)-butyric acid A solution of the product of the previous step (159 mg, 0.36 mmol), methanol (1.5 mL), water (0.20 mL) and 10 N NaOH (0.21 mL, 2.1 mmol) was heated at 50° C. After 4 h, the reaction mixture was cooled to room temperature, diluted with 50% aqueous acetic acid, and purified by preparative HPLC to give the title compound as the TFA salt (110 mg, 58% yield over 2 steps). (m/z): [M+H] calcd for C$_{26}$H$_{41}$NO$_4$, 432.31; found, 432.8. $^1$H NMR (CD$_3$OD, 400 mHz) δ (ppm): 6.97 (d, J=8.2 Hz, 1H), 6.65 (dd, J=8.4, 2.5 Hz, 1H), 6.62 (d, J=2.4 Hz, 1H), 4.01 (m, 1H), 3.48 (s, 3H), 3.47-3.37 (m, 3H), 3.22 (m, 1H), 2.58 (dd J=15.9, 10.2 Hz, 2H), 2.10 (m, 1H), 1.97 (m, 2H), 1.82-1.60 (m, 10H), 1.37-1.18 (m, 6H), 0.92 (m, 2H), 0.80 (t, J=7.4 Hz, 3H), 0.71 (t, J=7.2 Hz, 3H).

Example 13

(S)-2-Cyclohexylmethyl-4-((2R,3R)-1,1-diethyl-7-hydroxy-3-methoxy-1,2,3,4-tetrahydro-naphthalen-2-ylamino)-butyric acid Following the procedure of Example 12 using (6R,7R)-7-amino-8,8-diethyl-6-methoxy-5,6,7,8-tetrahydro-naphthalen-2-ol hydrochloride in step (a), the title compound was prepared. (m/z): [M+H] calcd for C$_{26}$H$_{41}$NO$_4$, 432.31. found, 432.8. $^1$H NMR (CD$_3$OD, 400 mHz) δ (ppm): 6.97 (d, J=8.2 Hz, 1H), 6.65 (dd, J=8.3, 2.5 Hz, 1H), 6.62 (d, J=2.6 Hz, 1H), 4.01 (m, 1H), 3.48 (s, 3H), 3.47-3.37 (m, 3H), 3.20 (m, 1H), 2.58 (dd J=16.0, 10.0 Hz, 2H), 2.13-1.95 (m, 2H), 1.95-1.60 (m, 10H), 1.38-1.19 (m, 6H), 0.92 (m, 2H), 0.80 (t, J=7.4 Hz, 3H), 0.71 (t, J=7.3 Hz, 3H).

Example 14

(R)-2-Cyclohexylmethyl-4-((2S,3S)-1,1-diethyl-7-hydroxy-3-methoxy-1,2,3,4-tetrahydro-naphthalen-2-ylamino)-butyric acid a. (R)-2-Cyclohexylmethyl-4-((2S,3S)-1,1-diethyl-7-hydroxy-3-methoxy-1,2,3,4-tetrahydro-naphthalen-2-ylamino)-butyric acid methyl ester (6S,7S)-7-Amino-8,8-diethyl-6-methoxy-5,6,7,8-tetrahydro-naphthalen-2-ol hydrochloride salt (100 mg, 0.35 mmol), (R)-2-cyclohexylmethyl-4-oxo-butyric acid methyl ester (90 mg, 0.42 mmol) and triethylamine (35 mg, 0.035 mmol) were dissolved in dichloromethane (2.0 mL) and stirred at room temperature for 30 min. Sodium triacetoxyborohydride (1.03 g, 4.85 mmol) was added and the reaction was monitored by HPLC. After 3 h, additional (R)-2-cyclohexylmethyl-4-oxo-butyric acid methyl ester (20 mg, 0.1 mmol) and sodium triacetoxyborohydride (30 mg, 0.14 mmol) were added. Thirty minutes after the last addition, EtOAc (15 mL) was added and the mixture was washed with 5% aqueous sodium carbonate (2×5 mL) and saturated sodium chloride (5 mL).

The organic layer was dried with Na$_2$SO$_4$) and concentrated to give the title compound (190 mg). (m/z): [M+H]$^+$ calcd for C$_{27}$H$_{43}$NO$_4$, 446.33. found, 446.6.

b. (R)-2-Cyclohexylmethyl-4-((2S,3S)-1,1-diethyl-7-hydroxy-3-methoxy-1,2,3,4-tetrahydro-naphthalen-2-ylamino)-butyric acid Following the procedure of Example 12 step (b), the TFA salt of the title compound was isolated. (m/z): [M+H]$^+$ calcd for C$_{26}$H$_{41}$NO$_4$, 432.31. found, 432.8. $^1$H NMR (CD$_3$OD, 400 mHz) δ (ppm): 6.97 (d, J=8.5 Hz, 1H), 6.65 (dd, J=8.3, 2.3 Hz, 1H), 6.62 (d, J=2.3 Hz, 1H), 4.01 (m, 1H), 3.48 (s, 3H), 3.47-3.37 (m, 3H), 3.22 (m, 1H), 2.58 (dd J=16.0, 10.0 Hz, 2H), 2.15-1.95 (m, 2H), 1.95-1.60 (m, 10H), 1.38-1.18 (m, 6H), 0.92 (m, 2H), 0.80 (t, J=7.6 Hz, 3H), 0.71 (t, J=7.5 Hz, 3H).

Example 15

(R)-2-Cyclohexylmethyl-4-((2R,3R)-1,1-diethyl-7-hydroxy-3-methoxy-1,2,3,4-tetrahydro-naphthalen-2-ylamino)-butyric acid Following the procedure of Example 14 using (6R,7R)-7-amino-8,8-diethyl-6-methoxy-5,6,7,8-tetrahydro-naphthalen-2-ol hydrochloride in step (a), the title compound was prepared. (m/z): [M+H]$^+$ calcd for C$_{26}$H$_{41}$NO$_4$, 432.31. found, 432.8. $^1$H NMR (CD$_3$OD, 400 mHz) δ (ppm): 6.97 (d, J=8.2 Hz, 1H), 6.65 (dd, J=8.5, 2.5 Hz, 1H), 6.62 (d, J=2.3 Hz, 1H), 4.01 (m, 1H), 3.48 (s, 3H), 3.47-3.37 (m, 3H), 3.22 (m, 1H), 2.58 (dd J=15.7, 10.2 Hz, 2H), 2.10 (m, 1H), 1.98 (m, 2H), 1.79-1.60 (m, 10H), 1.37-1.18 (m, 6H), 0.92 (m, 2H), 0.80 (t, J=7.4 Hz, 3H), 0.71 (t, J=7.2 Hz, 3H).

Example 16

Following the procedure of Example 9 using the appropriate methyl ester in place of (S)-2-pentyl-4-oxo-butyric acid methyl ester and the racemic compound trans-7-amino-8,8-dimethyl-6-methoxy-5,6,7,8-tetrahydro-naphthalene-2-carboxylic acid amide.hydrochloride, the TFA salts of the following compounds were prepared:

16-A: trans-(S)-4-(7-Carbamoyl-1,1-dimethyl-3-methoxy-1,2,3,4-tetrahydro-naphthalen-2-ylamino)-2-cyclohexylmethyl-butyric acid: (m/z): [M+H]$^+$ calcd for C$_{25}$H$_{38}$N$_2$O$_4$, 431.28. found, 431.2

16-B: trans-(S)-4-(7-Carbamoyl-3-methoxy-1,1-dimethyl-1,2,3,4-tetrahydro-naphthalen-2-ylamino)-2-cyclohexyl-butyric acid: (m/z): [M+H]$^+$ calcd for C$_{24}$H$_{36}$N$_2$O$_4$, 417.27. found, 417.4.

Example 17

(S)-4-(2S,3S)-7-Carbamoyl-1,1-diethyl-3-methoxy-1,2,3,4-tetrahydro-naphthalen-2-ylamino)-2-cyclohexylmethyl-butyric acid a. (S)-4-((2S,3S)-7-Carbamoyl-1,1-diethyl-3-methoxy-1,2,3,4-tetrahydro-naphthalen-2-ylamino)-2-cyclohexylmethyl-butyric acid benzyl ester hydrochloride To a suspension of sodium (S)-3-benzyloxycarbonyl-4-cyclohexyl-1-hydroxy-butane-1-sulfonate (160 g, 400 mmol), the product of Preparation 17, in MeTHF (2.0 L) and water (600 mL) was added 1.0 M NaOH in water (400 mL)

and the reaction mixture was stirred at room temperature for 90 min. Phases were separated and the solution was concentrated to a volume of ~300 mL.

The resulting concentrated solution was added to a slurry of (6S,7S)-7-amino-8,8-diethyl-6-methoxy-5,6,7,8-tetrahydro-naphthalene-2-carboxylic acid amide hydrochloride (100.0 g, 319.7 mmol) in DMF (1 L). Resulting slurry was stirred at room temperature for 2 h, the reaction mixture was cooled to 0° C. followed by portion-wise addition of sodium triacetoxyborohydride (169 g, 799 mmol) over 15 min. The reaction mixture was stirred at RT overnight, cooled to 10° C. and then 1.0 M NaOH in water (3 L) and ethyl acetate (5 L) were added. The reaction mixture was stirred for 10 min, phases were separated, and the organic layer was washed with diluted brine (1:1, 2 L). To the organic layer was added 1.0 M HCl in water (520 mL, 520 mmol) and most of the ethyl acetate was removed by rotary evaporation. Water (500 mL) and ethanol (1 L) were added and the volume was slowly reduced by rotary evaporation to ~1 L. The resulting off-white free-flowing slurry was stirred at RT overnight. Product was isolated by filtration, flask and filter cake were washed with water (2×200 mL) and then dried to yield the title compound (175 g) as a white solid (~99% purity, 90% yield based on aminotetralin reagent). $^1$H NMR (400 MHz, DMSO-$d_6$): δ (ppm) 9.33 (br, 1H), 8.09 (br, 1H), 7.98 (s, 1H), 7.70 (s, 1H), 7.68 (d, 1H), 7.28-7.36 (m, 2H), 7.19 (d, 1H), 5.10 (q, 2H), 4.04 (m, 1H), 3.45 (dd, 1H), 3.38 (s, 3H), 3.25 (m, 2H), 3.05 (m, 1H), 2.62 (m, 2H), 1.95-2.15 (m, 2H), 1.61-1.82 (m, 3H), 1.50-1.61 (m, 4H), 1.42-1.50 (m, 1H), 1.24-1.32 (m, 1H), 0.98-1.18 (m, 4H), 0.71-0.89 (m, 2H), 0.63 (t, 3H), 0.52 (t, 3H).

b. (S)-4-((2S,3S)-7-Carbamoyl-1,1-diethyl-3-methoxy-1,2,3,4-tetrahydro-naphthalen-2-ylamino)-2-cyclohexylmethyl-butyric acid The product of the previous step (175.0 g, 299 mmol) was partitioned between ethyl acetate (2.5 L), water (1 L) and 1.0 M NaOH in water (300 mL, 299 mmol). Phases were separated, the organic layer was washed with diluted brine (1:1, 250 mL), and dried with sodium sulfate. Solvent was removed by rotary evaporation and the resulting product dried overnight under high vacuum to provide the free-base intermediate (S)-4-((2S,3S)-7-carbamoyl-1,1-diethyl-3-methoxy-1,2,3,4-tetrahydro-naphthalen-2-ylamino)-2-cyclohexylmethyl-butyric acid benzyl ester (~160 g) as a sticky solid.

The free-base intermediate was dissolved in a mixture of acetonitrile (1.6 L) and water (300 mL). To half of the solution (1 L) was added 10% palladium (10 g, 9 mmol) on carbon (wet). The reaction mixture was purged with nitrogen and then with hydrogen for 2 min and then exposed to 10-15 psi $H_2$ for 3 h at RT. The reaction mixture was filtered through celite, and the flask and filter cake were washed with acetonitrile (50 mL). The yellowish filtrate was stirred with thiol-modified silica (10 g) at RT for 2 h and then filtered through celite. Most of the solvent was removed by rotary evaporation at 25° C. Acetonitrile (500 mL) was added and most of the solvent was removed by rotary evaporation. Additional acetonitrile (500 mL) was added resulting in fast precipitation of sticky solids. The reaction mixture was stirred vigorously at room temperature overnight resulting in a free-flowing off-white slurry. Product was isolated by filtration; the filter cake was washed with acetonitrile (2×50 mL) and then dried under vacuum to yield the title compound as a crystalline solid (56 g, 98.8% purity). Water content 0.49% (w/w). $^1$H NMR (400 MHz, DMSO-$d_6$): δ (ppm) 7.89 (br, 1H), 7.65 (s, 1H), 7.60 (d, 1H), 7.22 (br, 1H), 7.11 (d, 1H), 3.55 (m, 1H), 3.38 (s, 3H), 3.25 (dd, 1H), 2.95 (m, 1H), 2.59 (d, 1H), 2.49 (m, 2H), 1.81 (m, 2H), 1.49-1.63 (m, 5H), 1.41-1.50 (m, 2H), 1.05-1.25 (m, 4H), 0.72-0.90 (m, 2H), 0.45 (t, 3H), 0.57 (t, 3H).

Example 18

4-((2S,3S)-7-Carbamoyl-1,1-diethyl-3-methoxy-1,2,3,4-tetrahydro-naphthalen-2-ylamino)-2-(trans-4-hydroxy-cyclohexylmethyl)-butyric acid (A) and 4-((2S,3S)-7-Carbamoyl-1,1-diethyl-3-methoxy-1,2,3,4-tetrahydro-naphthalen-2-ylamino)-2-(cis-4-hydroxy-cyclohexylmethyl)-butyric acid (B)

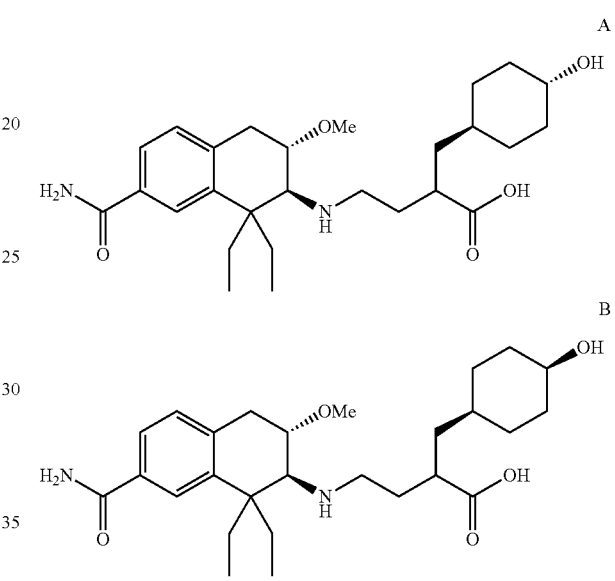

a. 2-[4-(tert-Butyl-dimethyl-silanyloxy)-cyclohexylmethylene]-succinic acid 1-methyl ester A solution of dimethyl succinate (730 mg, 5.0 mmol) and 4-(tert-butyl-dimethyl-silanyloxy)-cyclohexanecarbaldehyde (1.00 g, 4.1 mmol) was added over 25 min to a 1.0M solution of potassium tert-butoxide in tert-butanol (4.4 mL. 4.4 mmol). The reaction mixture was heated at 50° C. for 50 min, cooled to RT and concentrated under vacuum. The residue was dissolved in water (25 mL) and washed with EtOAc (2×10 mL). The aqueous layer was acidified with 6 N HCl (2.0 mL, 12 mmol) and extracted with EtOAc (2×20 mL), dried ($Na_2SO_4$) and concentrated. The crude product was purified by flash chromatography (25% EtOAc/DCM) to give the title compound (560 mg) as a mixture of olefin isomers (~1:1) and a mixture of cis and trans isomers at the cyclohexyl ring (~1:1). $^1$H NMR (CDCl$_3$, 400 mHz) δ (ppm) olefin peaks at 6.88 (d, J=10.2 Hz) 6.77 (d, J=10.0 Hz) CHOTBS peaks at 3.96 ppm (br s) (cis isomer, hydrogen equatorial, 3.55 (m) (trans isomer, hydrogen axial).

b. 2-[4-(tert-Butyl-dimethyl-silanyloxy)-cyclohexylmethyl]-succinic acid 1-methyl ester To a solution of the product of the previous step (560 mg, 1.6 mmol) in EtOAc (15 mL) was added 10% Pd/C (50% water, 165 mg dry weight). The reaction was shaken under 50 psi hydrogen for 16 h. The reaction was filtered through Celite, rinsing with EtOAc (5×5 mL), MeOH (3×5 mL) and DCM (3×5 mL). The combined filtrates were concentrated to dryness at reduced pressure. The crude product was purified by flash chromatography (25% EtOAc/DCM) to give the title compound (245 mg) as a ~1:1 mixture of cis and trans isomers at the cyclohexyl ring. $^1$H NMR (CDCl$_3$, 400 mHz) δ (ppm) CHOTBS peaks at 3.92 ppm (br s) (cis isomer, hydrogen equitorial), 3.50 (m) (trans isomer, hydrogen axial)

c. 2-[4-(tert-Butyl-dimethyl-silanyloxy)-cyclohexyl-methyl]-4-hydroxy-butyric acid methyl ester A solution of the product of the previous step (245 mg, 0.683 mmol) in THF (2.0 mL) was cooled in ice and a solution of borane in 1.0 M THF (1.4 mL) was added over 5 min. The reaction was stirred at 0° C. for 1.5 h, and then quenched by the dropwise addition of MeOH (10 mL). The mixture was concentrated under reduced pressure. Additional MeOH (10 mL) was added and the mixture was concentrated under reduced pressure to give the crude title product (228 mg) which was used immediately in the next step.

d. 2-[4-(tert-Butyl-dimethyl-silanyloxy)-cyclohexyl-methyl]-4-oxo-butyric acid methyl ester The product of the previous step (228 mg, 0.66 mmol) was dissolved in DCM (7.0 mL). DMSO (218 mg, 2.8 mmol) and DIPEA (361 mg, 2.8 mmol) were added and the mixture was cooled to −10° C. Sulfur trioxide pyridine complex (223 mg, 1.4 mmol) was added as a solid, and the reaction was stirred at −10° C. for 1.5 h. DCM (20 mL) was added, followed by 0.5 N HCl (10 mL). Layers were separated and the aqueous layer was extracted with DCM (2×10 mL). The combined organic layers were washed with water (3×10 mL) and saturated NaCl (10 mL), then dried (Na$_2$SO$_4$) and concentrated to give the title compound (220 mg). $^1$H NMR (CDCl$_3$, 400 mHz) showed aldehyde peaks at 9.81 and 9.75 ppm.

e. 2-[4-(tert-Butyl-dimethyl-silanyloxy)-cyclohexyl-methyl]-4-((2S,3S)-7-carbamoyl-1,1-diethyl-3-methoxy-1,2,3,4-tetrahydro-naphthalen-2-ylamino)-butyric acid methyl ester A solution of (6S,7S)-7-amino-8,8-diethyl-6-methoxy-5,6,7,8-tetrahydro-naphthalene-2-carboxylic acid amide (100 mg, 0.32 mmol), the product of the previous step (140 mg, 0.41), triethylamine (33 mg, 0.33 mmol) in DCM (2.0 mL) and MeOH (0.5 mL) was stirred at RT for 35 min. Sodium triacetoxyborohydride (135 mg, 0.64 mmol) was added and the reaction was monitored by HPLC. Additional portions of sodium triacetoxyborohydride were added at 1 h (50 mg) and 1.5 h (100 mg), and an additional portion of the aldehyde was added at 1.75 h (80 mg). Fifteen minutes after the last addition, DCM (20 mL) and saturated NaHCO$_3$ (10 mL) were added. The layers were separated and the aqueous layer was extracted with DCM (2×10 mL). The combined organic extracts were dried (Na$_2$SO$_4$) and concentrated to give the crude title product (283 mg).

f. 4-((2S,3S)-7-Carbamoyl-1,1-diethyl-3-methoxy-1,2,3,4-tetrahydro-naphthalen-2-ylamino)-2-(trans-4-hydroxy-cyclohexylmethyl)-butyric acid methyl ester (f1) and 4-((2S,3S)-7-Carbamoyl-1,1-diethyl-3-methoxy-1,2,3,4-tetrahydro-naphthalen-2-ylamino)-2-(cis-4-hydroxy-cyclohexylmethyl)-butyric acid methyl ester (f2)

A portion of the crude product of the previous step (28 mg, 0.32 mmol) was dissolved in 50% aqueous AcOH (0.5 mL). After 16 h, the products were separated by preparative HPLC to give the title compounds.

f1 (first eluting) (3.3 mg) (m/z): [M+H]$^+$ calcd for C$_{28}$H$_{44}$N$_2$O$_5$ 489.33. found 489.6. $^1$H NMR (CD$_3$OD, 400 mHz) δ (ppm) 7.71 (d, J=1.6 Hz, 1H), 7.65 (d, J=8.0, 1H), 7.20 (d, J=8.0 Hz, 1H), 4.02 (m, 1H), 3.63 (s, 3H), 3.51 (dd, J=16.5, 5.5 Hz, 1H), 3.44 (s, 3H), 3.44-3.30 (m, 3H), 3.14 (m, 1H), 2.70 (m, 1H), 2.54 (m, 1H), 2.24 (m, 1H), 2.00-1.50 (m, 9H), 1.30 (m, 2H), 1.12 (m, 3H), 0.91 (m, 2H), 0.71 (t, J=7.5 Hz, 3H), 0.62 (t, J=7.2 Hz).

f2 (second eluting) (7.3 mg) (m/z): [M+H]$^+$ calcd for C$_{28}$H$_{44}$N$_2$O$_5$ 489.33. found 489.6. $^1$H NMR (CD$_3$OD, 400 mHz) δ (ppm) 7.71 (d, J=1.6 Hz, 1H), 7.65 (dd, J=8.0, 1.4 Hz, 1H), 7.20 (d, J=8.2 Hz, 1H), 4.02 (m, 1H), 3.79 (br s, 1H) 3.62 (s, 3H), 3.51 (dd, J=16.7, 5.7 Hz, 1H), 3.44 (s, 3H), 3.44-3.30 (m, 2H), 3.15 (m, 1H), 2.68 (m, 1H), 2.57 (m, 1H), 2.24 (m, 1H), 2.05-1.80 (m, 2H), 1.70-1.55 (m, 6H), 1.50-1.10 (m, 8H), 0.71 (t, J=7.4 Hz, 3H), 0.62 (t, J=7.3 Hz, 3H).

g. 4-((2S,3S)-7-Carbamoyl-1,1-diethyl-3-methoxy-1,2,3,4-tetrahydro-naphthalen-2-ylamino)-2-(trans-4-hydroxy-cyclohexylmethyl)-butyric acid (A)

To a solution of 4-((2S,3S)-7-carbamoyl-1,1-diethyl-3-methoxy-1,2,3,4-tetrahydro-naphthalen-2-ylamino)-2-(trans-4-hydroxy-cyclohexylmethyl)-butyric acid methyl ester (f1) (27.4 mg, 0.045 mmol) in MeOH (0.50 mL) was added water (32 μL) and 10N NaOH (32 μL, 0.32 mmol). The mixture was heated at 50° C. After 15 h, the reaction mixture was cooled to RT, dissolved in 50% aqueous AcOH (6 mL) and purified by preparative HPLC to give the title compound (13.8 mg) as a lyophylized powder. (m/z): [M+H] calcd for C$_{27}$H$_{42}$N$_2$O$_5$ 475.32. found 475.2. $^1$H NMR (CD$_3$OD, 400 mHz) δ (ppm) 7.78 (d, J=1.6 Hz, 1H), 7.72 (dd, J=8.0 Hz, 1.7 Hz, 1H), 7.28 (d, J=8.2 Hz, 1H), 4.09 (m, 1H), 3.57 (dd, J=16.7, 5.9 Hz, 1H), 3.52 (s, 3H), 3.52-3.42 (m, 3H), 3.23 (m, 1H), 2.78 (m, 1H), 2.58 (m, 1H), 2.31 (m, 1H), 2.05-1.60 (m, 10H), 1.40-1.15 (m, 4H), 1.00 (m. 2H), 0.79 (t, J=7.5 Hz, 3H), 0.70 (dt, J=7.3, 1.3 Hz, 3H).

h. 4-((2S,3S)-7-Carbamoyl-1,1-diethyl-3-methoxy-1,2,3,4-tetrahydro-naphthalen-2-ylamino)-2-(cis-4-hydroxy-cyclohexylmethyl)-butyric acid (B)

To a solution of 4-((2S,3S)-7-carbamoyl-1,1-diethyl-3-methoxy-1,2,3,4-tetrahydro-naphthalen-2-ylamino)-2-(cis-4-hydroxy-cyclohexylmethyl)-butyric acid methyl ester (f2) (56 mg, 0.11 mmol) in MeOH (0.50 mL) was added water (66 μL) and 10 N NaOH (66 μL, 0.66 mmol). The mixture was heated at 50° C. After 15 h, the reaction mixture was cooled to RT, dissolved in 50% aqueous AcOH (6 mL) and purified by preparative HPLC to give the title compound (54 mg) as a lyophylized powder. (m/z): [M+H] calcd for C$_{27}$H$_{42}$N$_2$O$_5$ 475.32. found 475.2. $^1$H NMR (CD$_3$OD, 400 mHz) δ (ppm) 7.78 (d, J=1.8 Hz, 1H), 7.72 (dd, J=8.0 Hz, 1.7 Hz, 1H), 7.28 (d, J=8.0 Hz, 1H), 4.09 (m, 1H), 3.88 (br s, 1H), 3.58 (dd, J=16.6, 5.6 Hz, 1H), 3.52 (s, 3H), 3.52-3.46 (m, 2H) 3.30-3.20 (m, 1H), 2.77 (m, 1H), 2.59 (m, 1H), 2.31 (m, 1H), 2.05-1.92 (m, 2H), 1.79-1.65 (m, 6H), 1.60-1.35 (m, 8H), 0.79 (t, J=7.5 Hz, 3H), 0.70 (dt, J=7.2, 1.6 Hz).

Example 19

Metabolite Study

A sample of (S)-4-((2S,3S)-7-carbamoyl-1,1-diethyl-3-methoxy-1,2,3,4-tetrahydro-naphthalen-2-ylamino)-2-cyclohexylmethyl-butyric acid, the compound of Example 1, was incubated for 4 h at 37° C. with cryopreserved human hepatocytes in DMSO at a concentration of 1.2 million cells/mL. Aliquots of the resulting solution were mixed with one volume of 97% acetonitrile/3% TFA and frozen at −20° C. Upon thawing, samples were centrifuged for 10 min at 20,800×g and 4° C. Supernatants were collected, diluted with 3 volumes of water and analyzed by HPLC coupled with mass spectrometry (LC/MS) under the conditions described below. For metabolite identification, aliquots after dilution were combined separately with compound A and with compound B of Example 18 and analyzed by LC/MS. The resulting ion extraction chromatograms at 475.3±0.5 a.m.u. are consistent with the interpretation that the principal hydroxyl metabolite of the compound of Example 1, is the trans-4-hydroxy compound A, although the cis-4-hydroxy compound B cannot be ruled out.

Agilent model 1100 HPLC with Luna C18(2) 100 A 5 μm column; flow rate: 0.25 mL/min; Solvent A: 95% water, 5% acetonitrile, 0.05% TFA; Solvent B: >95% acetonitrile, 5% water, 0.05% TFA; Gradient (time(min)/% B): 0/7, 5/7, 60/25, 61/100, 63.5/100, 64/7, 70/7. Applied Biosystems model API3000 triple quadrupole mass spectrometer.

Assay 1: Radioligand Binding Assay on Human Mu, Human Delta and Guinea Pig Kappa Opioid Receptors a. Membrane Preparation

CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin—100 μg/mL streptomycin and 800 μg/mL Geneticin in a 5% $CO_2$, humidified incubator @37° C. Receptor expression levels ($B_{max}$ ~2.0 and ~0.414 pmol/mg protein, respectively) were determined using [$^3$H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N'-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 μL containing the appropriate amount of membrane protein (~3, ~2 and ~20 μg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 μM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM naloxone. $K_i$ values for test compounds were calculated, in Prism, from the best fit $IC_{50}$ values, and the $K_d$ value of the radioligand, using the Cheng-Prusoff equation ($K_i = IC_{50}/(1+([L]/K_d))$ where [L]=the concentration of [$^3$H]-Diprenorphine Results are expressed as the negative decadic logarithm of the $K_i$ values, $pK_i$.

Test compounds having a higher $pK_i$ value in these assays have a higher binding affinity for the mu, delta, or kappa opioid receptor. The final compounds named in Examples 1-16 were tested in these assays. All of the compounds had a $pK_i$ value between about 8.7 and about 10.9 at the human mu opioid receptor. For example, the compounds of Examples 1, 9, 10-G, and 12 had $pK_i$ values of 9.4, 9.2, 9.6, and 9.7, respectively. Compounds of the invention also exhibited $pK_i$ values between about 7.5 and about 10.3 at the human delta and guinea pig kappa opioid receptors.

Assay 2: Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound [$^{35}$S]GTPγS present following receptor activation in membranes prepared from CHO-K1 cells expressing the human mu opioid receptor.

a. Mu Opioid Receptor Membrane Preparation

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 pmol/mg protein, respectively. Protein concentration was determined using a Bio-Rad Bradford Protein Assay kit. Membranes were stored in frozen aliquots at −80° C., until required.

b. Human Mu [$^{35}$S]GTPγS Nucleotide Exchange Assay

Membranes were prepared as described above, and prior to the start of the assay, aliquots were diluted to a concentration of 200 μg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 μM into Assay Buffer containing 0.1% BSA, and serial (1:5) dilutions then made to generate ten concentrations of compound ranging from 40 pM-80 μM. GDP and [$^{35}$S]GTPγS were diluted to 40 μM and 0.4 nM, respectively, in Assay Buffer. The assay was performed in a total volume of 200 μL containing 10 μg of membrane protein, test compound ranging from 10 pM-20 μM), 10 μM GDP, and 0.1 nM [$^{35}$S]GTPγS diluted in 10 mM MgCl$_2$, 25 mM NaCl, and 0.0125% BSA (final assay concentrations). A DAMGO (Tyr-D-Ala-Gly-(methyl)Phe-Gly-ol) concentration-response curve (ranging from 12.8 pM-1 μM) was included on every plate.

Assay plates were prepared immediately prior to assay following the addition of 50 μL of the NaCl/MgCl$_2$/GDP solution, 50 μL of test compound, and 50 μL of [$^{35}$S]GTPγS. The assay was initiated by the addition of 50 μL of membrane protein and allowed to incubate for 30 minutes at room temperature. The reaction was terminated by filtration onto 96-well GF/B filter plates, pre-blocked with 0.3% polyethylenimine, using a Packard Filtermate harvester, and wash with ice-cold Assay Buffer (3×200 μl). Plates are dried overnight prior to determination of counts bound via liquid scintillation on a Packard Topcount instrument. Vehicle: DMSO not to exceed 1% final assay concentration.

The amount of bound [$^{35}$S]GTPγS is proportional to the degree of activation of the mu opioid receptors by the test compound. The intrinsic activity (IA), expressed as a percentage, was determined as the ratio of the amount of bound [$^{35}$S]GTPγS observed for activation by the test compound to the amount observed for activation by DAMGO which is presumed to be a full agonist (IA=100). All of the carboxylic acid compounds of formula (I) were tested in this assay and demonstrated intrinsic activities of less than about 22. For example, the compounds of Examples 1, 9, 10-G, and 12 had IA values of −8, −2, 7, and −5, respectively. In addition, the esters of Examples 2, 4, 5, 6, and 7-A exhibited IA values of −5, 6, 17, 19, and 8, respectively. Thus, compounds of the present invention have been shown to act as antagonists at the human mu opioid receptor.

Assay 3: Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (©1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit ID$_{50}$ values were calculated. Curve minima and maxima were fixed to loperamide control values (indicating 0% reversal) and vehicle controls (indicating 100% reversal), respectively. Results are expressed as ID$_{50}$, the dose required for 50% reversal of the effects of loperamide, in milligrams per kilogram. The compounds of Examples 1, 9, 10-G, and 12 administered orally, exhibited ID$_{50}$ values of 0.09 mg/kg, 0.10 mg/kg, 0.12 mg/kg, and 0.05 mg/kg, respectively in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula 2:

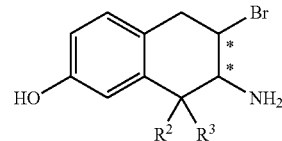

or a hydrobromide salt thereof, wherein R$^2$ and R$^3$ are each independently C$_{1-3}$alkyl, and the substituents at the chiral centers marked by asterisks are in the trans configuration.

2. A process for preparing a hydrobromide salt of a compound of formula 2 in solid form:

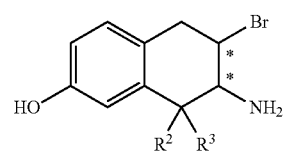

wherein R$^2$ and R$^3$ are each independently C$_{1-3}$alkyl, and the substituents at the chiral centers marked by asterisks are in the trans configuration, the process comprising:

reacting a racemic mixture of a compound of formula 1 and a compound of formula 1 having the opposite stereochemistry at the indicated chiral centers:

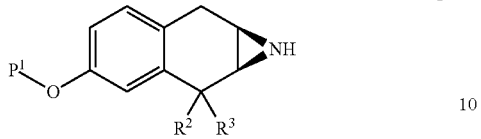

wherein $P^1$ is $C_{1-3}$ alkyl, with hydrogen bromide to form the hydrobromide salt of the compound of formula 2; and (b) isolating the hydrobromide salt of the compound of formula 2 in solid form.

3. The process of claim 2 wherein step (a) is performed in the presence of a phase transfer catalyst.

4. The compound of claim 1 wherein the compound is the hydrobromide salt of compound 2 in solid form.

* * * * *